US006713506B2

(12) United States Patent
Dou et al.

(10) Patent No.: US 6,713,506 B2
(45) Date of Patent: Mar. 30, 2004

(54) TEA POLYPHENOL ESTERS AND ANALOGS THEREOF FOR CANCER PREVENTION AND TREATMENT

(75) Inventors: Q. Ping Dou, Tampa, FL (US); Sangkil Nam, Tampa, FL (US); David M. Smith, Tampa, FL (US)

(73) Assignee: University of South Florida, Tampa, FL (US)

(*) Notice: Subject to any disclaimer, the term of this patent is extended or adjusted under 35 U.S.C. 154(b) by 0 days.

(21) Appl. No.: 09/973,834

(22) Filed: Oct. 11, 2001

(65) Prior Publication Data

US 2002/0151582 A1 Oct. 17, 2002

Related U.S. Application Data

(60) Provisional application No. 60/239,101, filed on Oct. 11, 2000.

(51) Int. Cl.[7] .................. A01N 43/16; A01N 43/08; A01N 39/00; A01N 43/32

(52) U.S. Cl. .............. 514/450; 514/452; 514/454; 514/455; 514/456; 514/457; 514/458; 514/461; 514/470; 514/471; 514/472; 514/473; 514/513; 514/529; 514/532

(58) Field of Search .................. 549/399; 514/452, 514/456, 457, 458, 461, 513, 521, 532, 450, 454, 455, 470, 471, 472, 473

(56) References Cited

U.S. PATENT DOCUMENTS 5,104,901 A * 4/1992 Shimamura et al. ........ 514/783
5,804,567 A * 9/1998 Cheng et al. ................ 514/49

OTHER PUBLICATIONS

Ahmad, S. et al. "Green Tea Ployphenol Epigallocatechin-3-gallate Inhibits the IL-1β-induced Activity and Expression of Cyclooxygenase-2 and Nitric Oxide Synthase-2 in Human Chondrocytes" *Free Redical Biology and Medicine*, 2002, vol. 33, No. 8, pp. 1097–1105.
An, B. et al. "Novel Dipeptidyl proteasome inhibitors overcome Bcl-2 protective function and selectively accumulate the cyclin-dependent kinase inhibitor p27 and induce apoptosis in transformed, but not normal, human fibroblasts" *Cell Death and Differentiation*, 1998, vol. 5, pp. 1062–1075.
Balasubramanian, S. et al. "Green Tea Polyphenol Stimulates a Ras, MEKK1, MEK3, and p38 Cascade to Increase Activator Protein 1 Factor-dependent Involucrin Gene Expression in Normal Human Keratinocytes" *The Journal of Biological Chemistry*, Jan. 18, 2002, vol. 277, No. 3, pp. 1828–1836.
Balentine, D. et al. "The Chemistry of Tea Flavonoids" *Critical Reviews in Food Science and Nutrition*, 1997, vol. 37, No. 8, pp. 693–704.

Baumeister, W. et al. The Proteasome: Paradigm of a Self-Compartmentalizing Protease, *Cell*, Feb. 6, 1998, vol. 92, pp. 367–380.
Chen, Z. et al. "Green tea epigallocatechin gallate shows a pronounced growth inhibitory effect on cancerous cells but not on their normal counterparts" *Cancer Letters*, 1998, vol. 129, pp. 173–179.
Dick, L. et al. "Mechanistic Studies on the Inactivation of the Proteasome by Lactacystin" *The Journal of Biological Chemistry*, Mar. 29, 1996, vol. 271, No. 13, pp. 7273–7276.
Fenteany, G. et al. "Inhibition of Proteasome Activities and Subunit-Specific Amino-Terminal Threonine Modification by Lactacystin" *Science*, May 5, 1995, vol. 268, pp. 726–731.
Fenteany, G. et al. "Lactacystin, Proteasome Function, and Cell Fate" *The Journal of Biological Chemistry*, Apr. 10, 1998, vol. 273, No. 15, pp. 8545–8548.
Fujiki, H. et al., "Green tea: cancer preventative beverage and/or drug" *Cancer Letters*, 2002, vol. 188, pp. 9–13.
Fujiki, H. et al. "Two stages of cancer prevention with green tea" *J Cancer Res Clin Oncol*, 1999, vol. 125, pp. 589–597.
Gazos Lopes, U. et al. "p53-dependent Induction of Apoptosis by Proteasome Inhibitors" *The Journal of Biological Chemistry*, May 16, 1997, vol. 272, No. 20, pp. 12893–12896.
Groll, M. et al. "Structure of 20S proteasome from yeast at 2.4A resolution" *Nature*, vol. 386, Apr. 3, 1997, pp. 463–471.
Gupta, S. et al. "Inhibition of prostate carcinogenesis in TRAMP mice by oral infusion of green tea polyphenols" *PNAS*, Aug. 28, 2001, vol. 98, No. 18, pp. 10350–10355.
Guttridge, D. et al. NF–kB Controls Cell Growth and Differentiation through Transcriptional Regulation of Cyclin D1" *Molecular and Cellular Biology*, Aug. 1999, pp. 5785–5799.
Heinemeyer, W. et al. "The Active Sites of the Eukaryotic 20 S Proteasome and the Involvement of Subunit Precursor Processing" *The Journal of Biological Chemistry*, Oct. 3, 1997, vol. 272, No. 40, pp. 25200–25209.
Hinz, M. et al. "NF–kB Function in Growth Control: Regulation of Cyclin D1 Expression and $G_0/G_1$–to–S–Phase Transition" *Molecular and Cellular Biology*, Apr. 1999, vol. 19, No. 4, pp. 2690–2698.
Hiipakka, R. et al. Structure–activity relationships for inhibition of human 5a–reductases by polyphenols *Biochemical Pharmacology*, 2002, vol. 63, pp. 1165–1176.

(List continued on next page.)

*Primary Examiner*—Alan L. Rotman
*Assistant Examiner*—Raymond Covington
(74) *Attorney, Agent, or Firm*—Saliwanchik, Lloyd & Saliwanchik

(57) ABSTRACT

Disclosed herein are ester-bond containing tea polyphenols that has a susceptibility to nucleophilic attack, their analogs and pharmaceutically acceptable salts, method for inhibiting proteasomal chymotrypsin-like activity in vivo and in vitro, methods for cancer treatment with tea-derived polyphenols, such as EGCG, ECG, GCG, or CG, as well as pharmaceutical compositions comprising the same.

15 Claims, 22 Drawing Sheets

OTHER PUBLICATIONS

Jodoin, J. et al. "Inhibition of the multidrug resistance P-glycoprotein activity by green tea polyphenols" *Biochimica et Biophysica Acta*, 2002, vol. 1542, pp. 149–159.

Katiyar, S. et al. "Prevention of UVB–induced immunosuppression in mice by the green tea polyphenol (—)-epigallocatechin-3-gallate may be associated with alterations in IL-10 and IL-12 production" *Carcinogenesis*, Nov. 1999, vol. 20, No. 11, pp. 2117–2124.

Kazi, A. et al. "Inhibition of Bcl–$X_L$ Phosphorylation by Tea Polyphenols or Epigallocatechin-3–Gallate is Associated with Prostrate Cancer Cell Apoptosis" *Molecular Pharmacology*, 2002, vol. 62, No. 4, pp. 765–771.

Kinjo, J. et al. "Activity–Guided Fractionation of Green Tea Extract with Antiproliferative Activity against Human Stomach Cancer Cells" *Biol. Pharm. Bull.*, 2002, vol. 25, No. 9, pp. 1238–1240.

Kubota, Y. et al. "Safety of Dietary Supplements: Chronotopic and Inotropic Effects on Isolated Rat Atria" *Biol. Pharm. Bull.*, 2002, vol. 25, No. 2, pp. 197–200.

Kuroda, Y. et al. "Antimutagenic and anticarcinogenic activity of tea polyphenols" *Mutation Research*, 1999, vol. 436, pp. 69–97.

Lamy, S. et al., "Green Tea Catechins Inhibit Vascular Endothelial Growth Factor Receptor Phosphorylation" *Cancer Research*, Jan. 15, 2002, vol. 62, pp. 381–385.

Lee, M. et al. "Pharmacokinetics of Tea Catechins after Ingestion of Green Tea and (—)-Epigallocatechin-3-gallate by Humans: Formation of Different Metabolites and Individual Variability" *Cancer Epidemiology*, Oct. 2002, vol. 11, pp. 1025–1032.

Levites, Y. et al. "Involvement of Protein Kinase C Activation and Cell Survival/Cell Cycle Genes in Green Tea Polyphenol (—)-Epigallocatechin-3-Gallate Neuroprotective Action" *The Journal of Biological Chemistry*, Aug. 23, 2002, vol. 277, No. 34, pp. 30574–30580.

Li, B. et al. "Bax degradation by the ubiquitin/proteasome–dependent pathway: Involvement in tumor survival and progression" PNAS, Apr. 11, 2000, vol. 97, No. 8, pp. 3850–3855.

Lin, Y. et al. "(—)-Epigallocatechin-3-gallate Blocks the Induction of Nitric Oxide Synthase by Down–Regulating Lipopolysaccaride–Induced Activity of Transcription Factor Nuclear Factor–kB" *Molecular Pharmacology*, 1997, vol. 52, pp. 465–472.

Loidi, G. et al. "Bivalency as a principle for proteasome inhibition" *Proc. Natl. Acad. Sci. USA*, May 1999, vol. 96, pp. 5418–5422.

Lu, Y. et al. "Topical Applications of caffeine or (—)-epigallocatechin gallate (EGCG) inhibit carcinogenesis and selectively increase apoptosis in UVB–induced skin tumors in mice" *PNAS*, Sep. 17, 2002, vol. 99, No. 19, pp. 12455–12460.

Maupin–Furlow, J. et al. "A Proteasome from the methanogenic Archaeon *Methanosarcina thermophila*" *The Journal of Biological Chemistry*, Dec. 1, 1995, vol. 270, No. 48, pp. 28617–28622.

Naasani, I. et al. "Telomerase Inhibition, Telomere Shortening, and Senescence of Cancer Cells by Tea Catechins" *Biochemical and Biophysical Research Communications*, 1998, vol. 249, pp. 391–396.

Nakagawa, T. et al. "Direct scavenging of nitric oxide and superoxide by green tea" *Food and Chemical Toxicology*, 2002, vol. 40, pp. 1745–1750.

Nam, S. et al. "Ester Bond–containing Tea Polyphenols Potently Inhibit Proteasome Activity in Vitro and in Vivo" *The Journal of Biological Chemistry*, Apr. 20, 2001, vol. 278, No. 16, pp. 13322–13330.

Nam, S et al. "Tannic Acid Potently Inhibits Tumor Cell Proteasome Activity Increases p27 and Bax Expression, and Induces $G_1$ Arrest and Apoptosis" *Cancer Epidemiology, Biomarkers & Prevention*, Oct. 2001, vol. 10, pp. 1083–1088.

Nicholson, D. et al. "Identification and inhibition of the ICE/CED-3 protease necessary for mammalian apoptosis" *Nature*, Jul 6, 1995, vol. 376, pp. 37–40.

Okabe, S. et al. "Mechanistic Aspects of Green Tea as a Cancer Preventive: Effect of Components on Human Stomach Cancer Cell Lines" *Jpn. J. Cancer Res.*, Jul. 1999, vol. 90, pp. 733–739.

Orner, G. et al. "Response of Apc–$^{min}$ and A33$^{N\Delta\beta-cat}$ mutant mice to treatment with tea, sulindac, and 2–amino–1–methyl–6–phenylimidazol[4,5–b]pyridine (PhIP)" *Mutation Research*, 2002, vol. 506–507, pp. 121–127.

Pianetti, S. et al. "Green Tea Polyphenol Epigallocatechin–3 Gallate Inhibits Her–2/Neu Signaling, Proliferation, and Transformed Phenotype of Breast Cancer Cells" *Cancer Research*, Feb. 1, 2002, vol. 62, pp. 652–655.

Ping Dou, Q. et al. "Proteasome inhibitors as potential novel anticancer agents" *Drug Resistance Updates*, 1999, vol. 2, pp. 215–223.

Sachinidis, A. et al. "Inhibition of the PDGF β–receptor tyrosine phosphorylation and its downstream intracellular signal transduction pathway in rat and human vascular smooth muscle cells by different catechins" *The FASEB Journal*, Jun. 2002, vol. 16, pp. 893–895.

Sanae, F. et al. "Effects of catechins on vascular tone in rat thoracic aorta with endothelium" *Life Sciences*, 2002, vol. 71, pp. 2553–2562.

Smith, D. et al. "A Novel β–Lactam Antibiotic Activates Tumor Cell Apoptotic Program by Inducing DNA Damage" *Mol Pharmacol*, 2002, vol. 61, No. 6, pp. 1348–1358.

Sun, J. et al. "CEP1612, a Dipeptidyl Proteasome Inhibitor, Induces p21$^{WAF1}$ and p27$^{K1P1}$ Expression and Apoptosis and Inhibits the Growth of the Human Lung Adenocarcinoma A–549 in Nude Mice" *Cancer Research*, Feb. 15, 2001, vol. 61, pp. 1280–1284.

Tosetti, F. et al. "Angioprevention: angiogenesis is a common and key target for cancer chemopreventive agents" *The FASEB Journal*, Jan. 2002, vol. 16, pp. 2–14.

Waltner–Law, M. et al. "Epigallocatechin Gallate, a Constituent of Green Tea, Represses Hepatic Glucose Production" *The Journal of Biological Chemistry*, Sep. 20, 2002, vol. 277, No. 38, pp. 34933–34940.

Weisburger, J. H. et al. "Mechanisms of chronic disease causation by nutritional factors and tobacco products and their prevention by tea polyphenols" *Food and Chemisty Toxicology*, 2002, vol. 40, pp. 1145–1154.

Yang, C. "Tea and Health" *Nutrition*, 1999, vol. 15, Nos. 11/12, pp. 946–949.

Yung, C. et al. "Human Salivary Tea Catechin Levels and Catechin Esterase Activities: Implication in Human Cancer Prevention Studies" *Cancer Epidemiology, Biomarkers & Prevention*, Jan. 1999, vol. 8, pp. 83–89.

* cited by examiner

Nam, Smith & Dou

Nam, Smith & Dou

L.

A

B

C

A

B

C

D

E

F

A

B

C

A

B

| R Groups | R' Groups |
|---|---|
| -H | =O |
| -OH | -H |
| -NH | -OH |
| -OMe | -NH2 |
| -CH2OH | OMe |
| -CH2NH2 | CH2OH |
| -GALLATE | CH2NH2 |
| | GALLATE |

10. 
11. 
12. 
13. 
14. 
15. 
16. 
17. 
18. 
19.

| Theaflavins | R | $R_1$ |
|---|---|---|
| Theaflavin 3-gallate | Gallate | H |
| Theaflavin 3'-gallate | H | Gallate |
| Theaflavin 3,3'-gallate | Gallate | Gallate |

Theasinensin A

Analogs of EGCG, R = $OCH_3$

| | |
|---|---|
| Sub only- | Substrate plus buffer |
| No Drug- | Proteasome, buffer, and substrate only |
| LLnV- | Peptide Proteasome inhibitor |

*EGCG-Epigallocatechingallate

MA-Methyl acetate

*MG-Methyl gallate

*GPA-Glucose pentaacetate

*BHB-Benzyl hydroxybenzoate

BGDB-butylene glycol dibenzoate

*ASP-Acetylsalicylic Acid

*- Significant difference

Gallate

MG-Methyl gallate

TEA POLYPHENOL ESTERS AND ANALOGS THEREOF FOR CANCER PREVENTION AND TREATMENT

The present application claims priority from U.S. provisional application Ser. No. 60/239,101 filed on Oct. 11, 2000, the disclosure of which is hereby incorporated by reference in its entirety.

FIELD OF THE INVENTION

The present invention relates to polyphenol esters derived from green and black teas, and analogs thereof, which are potent inhibitors of the growth of cancerous cells. Specifically, the invention relates to polyphenol esters that inhibit chymotrypsin-like, but not trypsin-like, proteasome activity, whereby tumor cells are arrested in $G_1$ phase and selective apoptosis of cancerous cells is promoted. Therefore, the invention relates to novel polyphenol esters and their use in the prevention and treatment of conditions characterized by abnormal cellular proliferation.

BACKGROUND OF THE INVENTION

Previous studies have suggested that tea consumption may have a protective effect against human cancer (Fujiki, 1999, *J Cancer Res Clin Oncol* 125:589–97; Kuroda et al., 1999, *Mutat Res* 436:69–97; Yang, 1999, *Nutrition* 15:946–9; Ahmad et al., 1999, *Nutr Rev* 57:78–83). The major components of green and black tea include epigallocatechin-3-gallate (EGCG), epigallocatechin (EGC), epicatechin-3-gallate (ECG), epicatechin (EC), and their epimers (see FIG. 1A).

Although tea-derived polyphenols affect numerous cancer-related proteins and have been shown to have anti-tumor property, their precise molecular targets have not been identified. The ubiquitin-proteasome system plays a critical role in the specific degradation of cellular proteins (Hochstrasser, 1995, *Curr Opin Cell Biol* 7:215–23), and one of the proteasome's functions is to protect tumor cells against apoptosis (Dou et al., 1999, *Drug Resistance Updates* 2:215–223). The chymotrypsin-like, but not trypsin-like, activity of the proteasome is associated with tumor cell survival (An et al., 1998, *Cell Death Differ* 5:1062–75; Lopes et al., 1997, *J Biol Chem* 272:12893–6).

The absence of specific knowledge of the molecular targets of tea-derived compounds having antitumor activities or activities directed against proliferative diseases has slowed development of more potent and specific analogs. Specifically, identification of the molecular target proteins of tea-derived compounds would facilitate development of better inhibitors through molecular modeling of the inhibitor-binding site.

Similarly, the absence of knowledge of the chemical features of such tea-derived compounds that are required for biological activity has also slowed development of improved analogs. In addition, knowledge of the specific targets of such tea-derived compounds permits rational design of cancer therapy and prevention strategies, where simultaneous manipulation of multiple metabolic pathways may be desirable.

SUMMARY OF THE INVENTION

As disclosed herein for the first time, the present invention provides means to address these problems. Herein, it is disclosed how ester-bond containing tea polyphenols potently inhibit the proteasomal chymotrypsin-like activity in vivo and in vitro. Treatment with tea-derived polyphenols is herein correlated with accumulation of cellular levels of both $p27^{KiP1}$ and IκB-α two natural proteasome substrates, and $G_1$-phase arrest of tumor cells.

In one embodiment, the present invention provides a method for inhibiting the proteasomal chymotrypsin activity. The inventive method comprises contacting the cell with an effective amount of a polyphenol ester having an ester bond that has a susceptibility to nucleophilic attack. Significantly, the method according to this invention does not inhibit the proteasomal trypsin activity in a cell. According to a preferred embodiment, the method of the present invention uses a tea-derived polyphenol compound, particularly, the polyphenol compound such as EGCG, ECG, GCG, or CG. According to another preferred embodiment, the polyphenol compound suitable for the instant invention is selected from the group consisting of formulae 1–29, as herein below described.

In another embodiment, the present invention provides for a method for treating or preventing cancer in a patient, comprising administering to the patient an effective amount of a polyphenol ester having an ester bond that has a susceptibility to nucleophilic attack. The inventive method is effective against major cancer types such as prostate cancer, breast cancer, lung cancer, colorectal cancer, bladder cancer, non-Hodgkin's lymphoma, uterine cancer, melanoma of the skin, kidney cancer, liver cancer, leukemia, ovarian cancer, and pancreatic cancer.

In yet another embodiment, the present invention discloses analogs of tea-derived polyphenols. Preferably, the analogs of tea-derived polyphenols of the present invention have the structure of formulae 1–28.

All these features and benefits of the present invention will become apparent to those of skill in the art upon reading the following disclosure.

DESCRIPTION OF THE FIGURES

FIG. 4C shows that EGCG does not significantly inhibit trypsin-like activity.

DETAILED DESCRIPTION OF THE INVENTION

Figure 1:
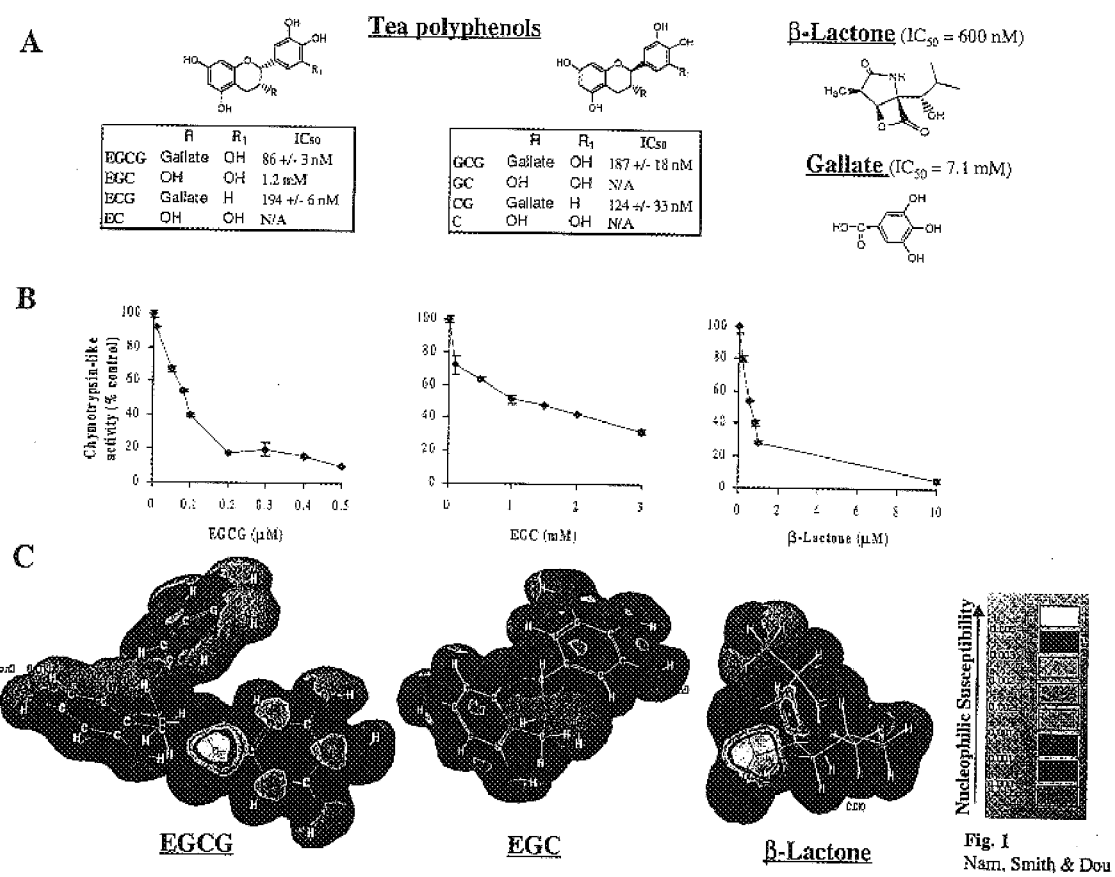
FIG. 1. Structure-activity relationships of tea polyphenols. A, structure and potency of polyphenols. $IC_{50}$ of each tea polyphenol towards the chymotrypsin-like activity of the 20S proteasome is measured as described in The Materials and Methods section of Example 1. N/A indicates that the inhibitory activity of the corresponding polyphenol at 50 μM is <10%. B, concentration-dependent inhibition of the chymotrypsin-like activity of the purified 20S proteasome by EGCG, EGC and β-lactone. C, The susceptibility of EGCG, EGC, and β-lactone to a nucleophilic attack.

The following abbreviations are used herein: EGCG, (-)-epigallocatechin-3-gallate; EGC, (-)-epigallocatechin;

ECG, (−)-epicatechin-3-gallate; EC, (−)-epicatechin; GCG, (−)-gallocatechin-3-gallate; CG, (−)-catechin-3-gallate; GC, (−)-gallocatechin; C, (−)-catechin; AMC, 7-amido-4-methyl-coumarin; PGPH, peptidyl-glutamyl peptide-hydrolyzing; DTT, dithiothreitol; HPLC, high-performance liquid chromatograph.

A skilled artisan would recognize that by "tea" it is meant an aqueous extract, usually with hot or cold water, of certain plant leaves. Many types of plants are suitable for tea preparation. Preferably, commercially available tea, i.e. dried and in certain instances, fermented leaves of the plant *Camellia sinesis* (green tea or black tea) is used. Many commercial tea products are decaffeinated, but are nevertheless suitable for the preparation of tea-derived polyphenol compounds of the instant invention.

The ubiquitin-proteasome system plays a critical role in the specific degradation of cellular proteins and one of the proteasome's functions is to protect tumor cells against apoptosis. It is shown herein that the major tea component epigallocatechin-3-gallate (EGCG) shows a pronounced growth inhibitory effect on breast and other cancer cells, but not on their normal counterparts. It is further shown that other tea-derived plant polyphenol compounds and their analogs have similar effects. Therefore, they are show to be as effective cancer preventative and therapeutic drugs with no or little toxicity.

We show that all tea polyphenols containing ester bonds, such as EGCG or epicatechin-3-gallate (ECG), potently inhibit proteasomal chymotrypsin-like, but not trypsin-like, activity in vitro ($IC_{50}$ 86–194 nM against a purified 20S proteasome) and in vivo (1–10 µM in Jurkat T cells), surprisingly and unexpectedly, at the concentrations found in the serum of green tea drinkers. In contrast, all the tea polyphenols without ester bonds, such as epigallocatechin (EGC) or epicatechin (EC), are not proteasome inhibitors. High-performance liquid chromatograph and atomic orbital energy analyses presented herein show that the carbon of the polyphenol ester bond is responsible for targeting and thereby inhibiting the proteasome in cancer cells. This inhibition of the proteasome in Jurkat T cells results in accumulation of two proteasome natural substrates, $p27^{KiP1}$ and IκB-α involved in inhibition of cell proliferation.

One breast cancer risk factor is an increased level of proteasomal activity that selectively degrades several tumor suppressor proteins. Inhibition of the proteasome activity by ester bond-containing tea polyphenols therefore contributes to the breast cancer-preventative and inhibitory activities of green tea and to a lesser extent black tea.

The extracts, compounds or combination of compounds derived therefrom are generally prepared by methods known in the art. Tea extracts containing high concentrations of EGCG, EGC, and other naturally occurring tea-derived polyphenols are commercially available, e.g. from Unilever N V, Rotterdam, Weena 455 3013 AL, Rotterdam, the Netherlands. With regard to chemical synthesis of the inventive compounds, reference is made Thompson et al., 1972, *J. Chem. Soc. Perkin Trans. I.*, 1287, for discussions on the synthesis on gallocatechin and catechin oligomers. The synthesis of EGCG is discussed extensively in Li et al., 2001, Enantioselective Synthesis of Epigallocatechin-3-gallate (EGCG), the Active Polyphenol Component from Green Tea, *Organic Letters*, 3:739–741. The disclosure of both of the above cited references is hereby incorporated in their entirety by reference.

Furthermore, while the invention is described with respect to tea-derived polyphenol compounds or analogs, from this disclosure the skilled organic chemist will appreciate and envision synthetic routes to obtain and/or prepare the active compounds. Accordingly, the invention comprehends synthetic tea polyphenols or their derivatives and/or their synthetic precursors which include, but are not limited to glycosides, gallates, esters, and the like. That is, the inventive compounds can be prepared from isolation from tea or from other plant species as well as from synthetic routes; and derivatives and synthetic precursors of the inventive compounds such as glycosides, gallates, esters, etc. are included in the inventive compounds.

With regard to the synthesis of the inventive compounds, the skilled artisan will be able to envision additional routes of synthesis, based on this disclosure and the knowledge in the art, without undue experimentation, for example, based upon a careful retrosynthetic analysis of the polymeric compounds, as well as the monomers. For instance, given the phenolic character of the inventive compounds, the skilled artisan can utilize various methods of selective protection/deprotection, coupled with organometallic additions, phenolic couplings and photochemical reactions, e.g., in a convergent, linear or biomimetic approach, or combinations thereof, together with standard reactions known to those well-versed in the art of synthetic organic chemistry, as additional synthetic methods for preparing the inventive compounds, without undue experimentation. In this regard, reference is made to W. Carruthers, Some Modern Methods of Organic Synthesis, 3rd ed., Cambridge University Press, 1986, and J. March, Advanced Organic Chemistry, 3rd ed., John Wiley & Sons, 1985, van Rensburg et al., Chem. Comm., 24: 2705–2706 (Dec. 21, 1996), Ballenegger et al., (Zyma SA) European Patent 0096 007 B 1, and documents in the References section below, all of which are incorporated herein by reference.

Formulations and Methods

Therefore, collectively, the inventive compounds, combinations thereof and compositions comprising the same have exhibited a wide array of activities against several aspects of cancer.

Hence, the compounds of the invention, combinations thereof and compositions containing the same are shown to be effective anti-cancer agents.

Formulations of the inventive compounds, combinations thereof and compositions comprising the same can be prepared with standard techniques well known to those skilled in the pharmaceutical, food science, medical and veterinary arts, in the form of a liquid, suspension, tablet, capsule, injectable solution or suppository, for immediate or slow-release of the active compounds.

A preferred carrier for the compounds of the invention, combinations thereof and compositions containing the same is water and the preparation is in the form of drinkable tea. The carrier may also be a polymeric delayed release system. Synthetic polymers are particularly useful in the formulation of a composition having controlled release. An early example of this was the polymerization of methyl methacrylate into spheres having diameters less than one micron to form so-called nano particles, reported by Kreuter, J., Microcapsules and Nanoparticles in Medicine and Pharmacology, M. Donbrow (Ed). CRC Press, p. 125–148.

A frequent choice of a carrier for pharmaceuticals and more recently for antigens is poly (d, 1-lactide-co-glycolide) (PLGA). This is a biodegradable polyester that has a long history of medical use in erodible sutures, bone plates and other temporary prostheses where it has not exhibited any toxicity. A wide variety of pharmaceuticals have been formulated into PLGA microcapsules. A body of data has accumulated on the adaption of PLGA for controlled, for example, as reviewed by Eldridge, J. H., et al. Current Topics in Microbiology and Immunology, 1989, 146:59–66. The entrapment in PLGA microspheres of 1 to 10 microns in diameter can have an effect when administered orally. The PLGA microencapsulation process uses a phase separation of a water-in-oil emulsion. The inventive compound or compounds is or are prepared as an aqueous solution and the PLGA is dissolved in suitable organic solvents such as methylene chloride and ethyl acetate. These two immiscible solutions are co-emulsified by high-speed stirring. A non-solvent for the polymer is then added, causing precipitation of the polymer around the aqueous droplets to form embryonic microcapsules. The microcapsules are collected, and stabilized with one of an assortment of agents (polyvinyl alcohol (PVA), gelatin, alginates, methyl cellulose) and the solvent removed by either drying in vacuo or solvent extraction.

Additionally, with regard to the preparation of slow-release formulations, reference is made to U.S. Pat. Nos. 5,024,843, 5,091,190, 5,082,668, 4,612,008 and 4,327,725, hereby incorporated herein by reference.

Compositions of the invention include one or more of the above noted compounds in a formulation having a pharmaceutically acceptable carrier or excipient, the inventive compounds having anti-cancer, anti-tumor or antineoplastic activities.

Another embodiment of the invention includes compositions comprising the inventive compounds or combinations thereof, as well as at least one additional antineoplastic, blood pressure reducing, antiinflammatory, antimicrobial, antioxidant and hematopoiesis agents, in addition to a pharmaceutically acceptable carrier or excipient.

Such compositions can be administered to a subject or patient in need of such administration in dosages and by techniques well known to those skilled in the medical, nutritional or veterinary arts taking into consideration the data herein, and such factors as the age, sex, weight, genetics and condition of the particular subject or patient, and the route of administration, relative concentration of particular oligomers, and toxicity (e.g., LD.sub.50).

The compositions can be co-administered or sequentially administered with other antineoplastic, anti-tumor or anti-cancer agents, antioxidants, DNA topoisomerase II enzyme inhibiting agents, inhibitors of oxidatively damaged DNA or cyclo-oxygenase and/or lipoxygenase, apoptosis, platelet aggregation, blood or in vivo glucose or NO or NO-synthase modulating agents, non-steroidal antiinflammatory agents and/or with agents which reduce or alleviate ill effects of antineoplastic, anti-tumor, anti-cancer agents, antioxidants, DNA topoisomerase II enzyme inhibiting agents, inhibitors of oxidatively damaged DNA, cyclo-oxygenase and/or lipoxygenase, apoptosis, platelet aggregation, blood or in vivo glucose or NO or NO-synthase modulating and/or non-steroidal antiinflammatory agents; again, taking into consideration such factors as the age, sex, weight, genetics and condition of the particular subject or patient, and, the route of administration.

Examples of compositions of the invention for human or veterinary use include edible compositions for oral administration, such solid or liquid formulations, for instance, capsules, tablets, pills and the like, as well as chewable solid or beverage formulations, to which the present invention may be well-suited since it is from an edible source (e.g., tea or tea-flavored solid or liquid compositions); liquid preparations for orifice, e.g. oral, nasal, anal, vaginal etc., administration such as suspensions, syrups or elixirs (including tea or tea-flavored compositions); and, preparations for parental, subcutaneous, intradermal, intramuscular or intravenous administration (e.g., injectable administration) such as sterile suspensions or emulsions. However, the active ingredient in the compositions may complex with proteins such that when administered into the bloodstream, clotting may occur due to precipitation of blood proteins; and, the skilled artisan should take this into account. In such compositions the active tea extract may be in admixture with a suitable carrier, diluent, or excipient such as sterile water, physiological saline, glucose, DMSO, ethanol, or the like. The active tea extract of the invention can be provided in lyophilized form for reconstituting, for instance, in isotonic aqueous, saline, glucose or DMSO buffer. In certain saline solutions, some precipitation may occur, and may be employed as a means to isolate inventive compounds, e.g., by a "salting out" procedure.

Kits

Further, the invention also comprehends a kit wherein the active tea-derived polyphenol compound is provided. The kit can include a separate container containing a suitable carrier, diluent or excipient. The kit can also include additional anti-cancer, anti-tumor or antineoplastic agent, antioxidant, DNA topoisomerase II enzyme inhibitor or an inhibitor of oxidative DNA damage or antimicrobial, or cyclo-oxygenase and/or lipoxygenase, NO or NO-synthase non-steroidal antiinflammatory, apoptosis and platelet aggregation modulating or blood or in vivo glucose modulating agent and/or an agent which reduces or alleviates ill effects of antineoplastic, anti-tumor or anti-cancer agents, antioxidant, DNA topoisomerase II enzyme inhibitor or antimicrobial, or cyclo-oxygenase and/or lipoxygenase, NO or NO-synthase, apoptosis, platelet aggregation and blood or in vivo glucose modulating and/or non-steroidal antiinflammatory agents for co- or sequential-administration. The additional agent(s) can be provided in separate container(s) or in admixture with the inventive polyphenol compounds. Additionally, the kit can include instructions for mixing or combining ingredients and/or administration.

The invention will be better understood by reference to the following examples which illustrate in a non-limiting manner the scope and application of the inhibition of cellular proliferation by polyphenol esters, which is the subject of the present invention.

EXAMPLE 1

Ester Bond-Containing Tea Polyphenols Potently Inhibit Proteasome Activity in vitro and in vivo It has been suggested that the proteasome is involved in tumor cell survival, and that tea consumption is correlated with cancer prevention. In this example, we show that ester bond-containing tea polyphenols potently and specifically inhibit the proteasome activity in vitro ($IC_{50}$ 86–194 nM) and in vivo (1–10 $\mu$M) at the concentrations found in the serum of green tea drinkers. As disclosed herein, high-performance liquid chromatograph and atomic orbital energy analyses show that the carbon of the polyphenol ester bond is responsible for targeting and thereby inhibiting the proteasome in cancer cells. This inhibition of the proteasome in tumor cells results in accumulation of two proteasome natural substrates, $p27^{Kip1}$ and I$\kappa$B-$\alpha$, and growth arrest in the $G_1$ phase of the cell cycle. Transformed cells are much more sensitive to ester bond-containing tea polyphenols than normal human cells. This example shows that the proteasome is a molecular target of tea polyphenols and that inhibition of the proteasome activity by ester bond-containing polyphenols is responsible for the cancer preventative effect of tea.

Materials and Methods

Inhibition of the proteasome activity in vitro by tea polyphenols—To measure the 20S proteasome chymotrypsin-like activity, 0.5 μg of a purified 20S proteasome (Calbiochem) is incubated with 20 μM of a fluorogenic peptide substrate, Suc-Leu-Leu-Val-Tyr-AMC (Calbiochem), for 30 min at 37° C. in 100 μl of assay buffer (20 mM Tris-HCl, pH 8.0), with or without tea polyphenols (purity >95%; Sigma) or tea extract. After incubation, the reaction mixture is diluted to 200 μl with the assay buffer, followed by measurement of the hydrolyzed 7-amido-4-methyl-coumarin (AMC) groups using a VersaFluor™ Fluorometer with an excitation filter of 380 nm and an emission filter of 460 nm (Bio-Rad). The green tea extract (a gift from Lipton Co., a subsidiary of Unilever NV) contained 51.5% EGCG, 14.7% ECG, 8.3% EGC, 8.5% EC, 4.4% (–)-gallocatechin-3-gallate (GCG), 2.4% (–)-gallocatechin (GC), 1.6% (–)-catechin (C), and 1.6% caffeine, while the black tea extract (a gift from Lipton Co., a subsidiary of Unilever NV) contained 19.7% EGCG, 14.9% ECG, 0.9% EGC, 4.8% EC, 0.0% GCG, 0.5% GC, 2.0% C, and 1.2% caffeine.

Cell culture and cell free extract preparation—Human Jurkat T, LNCaP prostate cancer, and PC-3 prostate cancer cells are cultured in RPMI 1640, and MCF7 is cultured in Dulbecco's modified Eagle's medium (DMEM). All the cell lines are supplemented with 10% fetal calf serum, 100 units/ml of penicillin, and 100 μg/ml of streptomycin at 95% humidity and 5% $CO_2$ at 37° C. A whole cell extract is prepared in a lysis buffer as described previously (An et al., (1998) *Cell Death Differ* 5(12), 1062–75). Briefly, cells are harvested and then washed PBS twice and homogenized in a lysis buffer (50 mM Tris-HCl, pH 8.0, 5 mM EDTA, 150 mM NaCl, 0.5% NP-40, 0.5 mM PMSF, and 0.5 mM DTT) for 30 min at 4° C. Then, the lysates are centrifuged at 20,000×g for 30 min and the supernant is collected for whole cell-free extracts.

Inhibition of the proteasome activity with cell free extracts by tea polyphenols—The whole cell extract (3.5 μg) from Jurkat T cells is incubated for 90 min at 37° C. with 20 μM of a fluorogenic peptide substrate, Suc-Leu-Leu-Val-Tyr-AMC (for the chymotrypsin-like activity), Z-Leu-Leu-Glu-AMC [peptidyl-glutamyl peptide-hydrolyzing (PGPH) activity; Calbiochem], and Z-Gly-Gly-Arg-AMC (for the trypsin-like activity; Bachem), in 100 μl of the assay buffer with or without 10 μM EGCG or EGC. The hydrolyzed AMCs are quantified as described above.

Inhibition of the proteasome activity in living cells by tea polyphenols—To measure inhibition of the chymotrypsin-like activity in living tumor cells, Jurkat T (1×10⁵ cells/ml/well), MCF7 or PC-3 cells (1×10⁴ cells/ml/well) are cultured in 24-well plates. These cells are first incubated for 12 h with various concentrations of EGCG, EGC, β-lactone or LLnL, followed by an additional 2 h-incubation with fluorogenic peptide substrates, Suc-Leu-Leu-Val-Tyr-AMC for the chymotrypsin-like activity and Z-Gly-Gly-Arg-AMC for the trypsin-like activity. After that, cell medium (200 μl per sample) is collected and used for measurement of free AMCs.

Calpain I and Caspase-3 activities assays with tea polyphenols—To measure calpain I activity, 3 μg purified calpain I (Human Erythrocytes, Calbiochem) is incubated with 40 μM of a fluorogenic peptide substrate, Suc-Leu-Tyr-AMC (Calbiochem), for 30 min at 37° C. in 100 μl of assay buffer (50 mM Tris-HCl, pH 7.5, containing 50 mM NaCl, 1 mM EDTA, 1 mM EGTA, 5 mM β-Mercaptoethanol, 5 mM $CaCl_2$, and 0.1% CHAPS), with or without EGCG. After incubation, the reaction mixture is diluted to 200 μl with the assay buffer, and the hydrolyzed AMCs are quantified as described above. For caspase-3 activity assay, the whole cell extract (3.5 μg) from Jurkat T cells is incubated for 90 min at 37° C. with 20 μM of a fluorogenic peptide substrate, Ac-Asp-Glu-Val-Asp-AMC. These procedures were similar to those of the proteasome assay with cell free extracts described above.

Atomic orbital energy analysis—The electron density surface colored by nucleophilic susceptibility is created using Cache Worksystem ver. 3.2™ (Oxford Molecular Ltd.). After geometrical optimization (using augmented MM3™), the electron distribution between the highest occupied molecular orbital and the lowest unoccupied molecular orbital is evaluated and a three-dimensional isosurface of susceptibility to nucleophilic attack (generated by an Extended Huckel wave function) is calculated and superimposed over the molecule. A colored "bullseye" with a white center is characteristic of atoms that are highly susceptible to nucleophilic attack.

HPLC analysis—EGCG, EGC or gallic acid (1 mM) is incubated with the purified 20S proteasome (45 μg) for the indicated hrs at 37° C. in 100 μl of a reaction buffer [20 mM Tris-HCl, 1 mM dithiothreitol (DTT), pH 7.2]. Similarly, ECG (0.5 mM) is incubated for 12 h with the 20S proteasome. After each reaction, the sample is filtered with a 0.45 μm nylon syringe filter (Nalge Co.), and 20 μl of filtered sample is injected to high-performance liquid chromatograph (HPLC) equipped with a C-18 reverse phase column (0.46×25 cm; Separation Group). The solvent system is 12% acetonitrile, 2% ethyl acetate and 0.05% phosphoric acid, the flow rate is 1 ml/min, and the proteasome cleavage products are monitored at 280 nm.

Western blot analysis—Western blot assay is performed as described previously (An et al., (1998) *Cell Death Differ* 5(12), 1062–75) using specific antibodies to $p27^{Kip}$ (monoclonal; Pharmingen), IκB-α (polyclonal; Santa Cruz), ubiquitin (polyclonal; Sigma) or actin (polyclonal; Santa Cruz). In brief, Jurkat T or LNCaP cells are treated with EGCG or EGC in dose-response or time-dependent manner. Cells are harvested and lysated using the whole lysis buffer. Cell lysates (70 μg) are separated by a sodium dodecyl sulfate-polyacrylamide gel electrophoresis (SDS-PAGE) and then, electrophoretically transferred to a nitrocellulose membrane. Immunocomplexes are detected using the ECL detection reagents kit (Amersham, Piscataway, N.J.).

Cell cycle analysis—Cell cycle analysis based on DNA content is performed as follows. Cells are harvested, counted and washed twice with PBS. Cells (5×10⁶) are then suspended in 0.5 ml PBS, pipetted and fixed in 5 ml of 70% ethanol for at least 2 h at −20° C. Cells are centrifuged, resuspended in 1 ml of propidium iodide staining solution (50 μg propidium iodide, 100 units RNase A and 1 mg glucose per ml PBS) and incubated at room temperature for 30 min. The cells are then analyzed with FACScan (Becton Dickinson Immunocytometry, CA.), ModFit LT and Win-MDI V.2.8 cell cycle analysis software (Verity Software, Topsham, Me.). The cell cycle distribution is shown as the percentage of cells containing $G_1$, S, $G_2$, and M DNA judged by propidium iodide staining.

Results

Lactacystin, when converted to its active form clastolactacystin β-lactone (β-lactone), is a highly specifica and irreversible inhibitor of the proteasome (Fenteany et al. (1998) *J Biol Chem* 273(15), 8545–8; Fenteany et al., (1995) *Science* 268(5211), 726–31; Dick et al. (1996) *J Biol Chem* 271(13), 7273–6). This β-lactone contains an ester bond (FIG. 1A) that is responsible for interacting with and inhibiting the proteasome (Fenteany et al. (1998) *J Biol Chem* 273(15), 8545–8; Fenteany et al., (1995) *Science* 268(5211), 726–31; Dick et al. (1996) *J Biol Chem* 271(13), 7273–6). It was an inventive contribution of the present inventors to notice a similar ester bond present in several tea polyphenols, including EGCG, ECG, (−)-gallocatechin-3-gallate (GCG), and (−)-catechin-3-gallate (CG) (FIG. 1A). We now show herein that tea polyphenols containing ester bonds inhibit the proteasome activity, whereas tea polyphenols without ester bonds do not. Thus, a cell-free proteasome activity assay is performed in the presence of tea polyphenols. The chymotrypsin-like activity of purified 20S proteasome, the catalytic core of 26S proteasome (see Hochstrasser, (1995) *Curr Opin Cell Biol* 7(2), 215–23), is significantly inhibited by EGCG (FIG. 1B), whose $IC_{50}$ value is calculated to be 86 nM (FIG. 1A). In contrast, EGC ($IC_{50}$ 1.2 mM) and gallic acid ($IC_{50}$ 7.1 mM), the two moieties of EGCG linked by an ester bond but each separately lacking an ester bond, are 14,000- and 83,000-fold less potent than EGCG, respectively (FIGS. 1A and B). As a positive control, β-lactone also potently inhibits the proteasomal chymotrypsin activity ($IC_{50}$ 600 nM; FIGS. 1A and B). The inhibition curve of EGCG is similar to that of β-lactone (FIG. 1B). Three other ester bond-containing tea polyphenols, ECG, GCG and CG (FIG. 1A), are also found to be strong inhibitors of the chymotrypsin-like activity of the purified 20S proteasome ($IC_{50}$ values were 194, 187, and 124 nM, respectively). In contrast, all the corresponding polyphenols that do not contain ester bonds, EC, GC, and C (FIG. 1A), do not inhibit the proteasome activity. These results indicate that the ester bond contained in tea polyphenols is essential for potent inhibition of the proteasome chymotrypsin-like activity. Furthermore, a green or black tea extract, which contains significant portions of EGCG (51.5% and 19.7%, respectively) and ECG (14.7% and 14.9%, respectively), also greatly inhibits the chymotrysin-like activity of the 20S proteasome ($IC_{50}$ values are 0.1 and 0.3 μg/ml, respectively).

The electrophilic ester bond carbon in β-lactone is hereby shown to be responsible for its biological inhibition of the proteasome. When the atomic orbital energy is analyzed, this ester bond carbon showed a high susceptibility towards a nucleophilic attack with a value of 1.1 (FIG. 1C). The levels of nucleophilic susceptibility found in tea polyphenols correlate with their proteasome inhibitory activities. The ester bond carbon of EGCG has the highest susceptibility towards a nucleophilic attack among all the other atoms, with a value of 0.7, whereas the carbon with the highest nucleophilic susceptibility on EGC is found to have a low value of 0.2 (FIG. 1C). Furthermore, high nucleophilic susceptibility is found in other ester bond-containing polyphenols, ECG, GCG, and CG (all with values of 0.7), whereas low nucleophilic susceptibility is found in non-ester bond polyphenols, EC, GC, and C (with values of 0.3, 0.2, and 0.3, respectively). Thus, the nucleophilic susceptibility of tea polyphenols correlates with their ability to inhibit the proteasome chymotrypsin-like activity.

The ester bond carbon in β-lactone can be attacked by the strong nucleophilic hydroxyl group of N-terminal threonine residue of the proteasome, forming a covalent complex. Similarly, the ester bond carbon in EGCG is also be attacked by the proteasome, forming an EGCG-proteasome complex. After binding of EGCG to the proteasome, the ester bond of EGCG is herein disclosed to be slowly cleaved. Disappearance of a high level of EGCG therefore occurs before, or associated with, appearance of low levels of gallic acid and EGC. To show this, highly purified EGCG is incubated with purified 20S proteasome for various times, followed by HPLC analysis.

Figure 2:
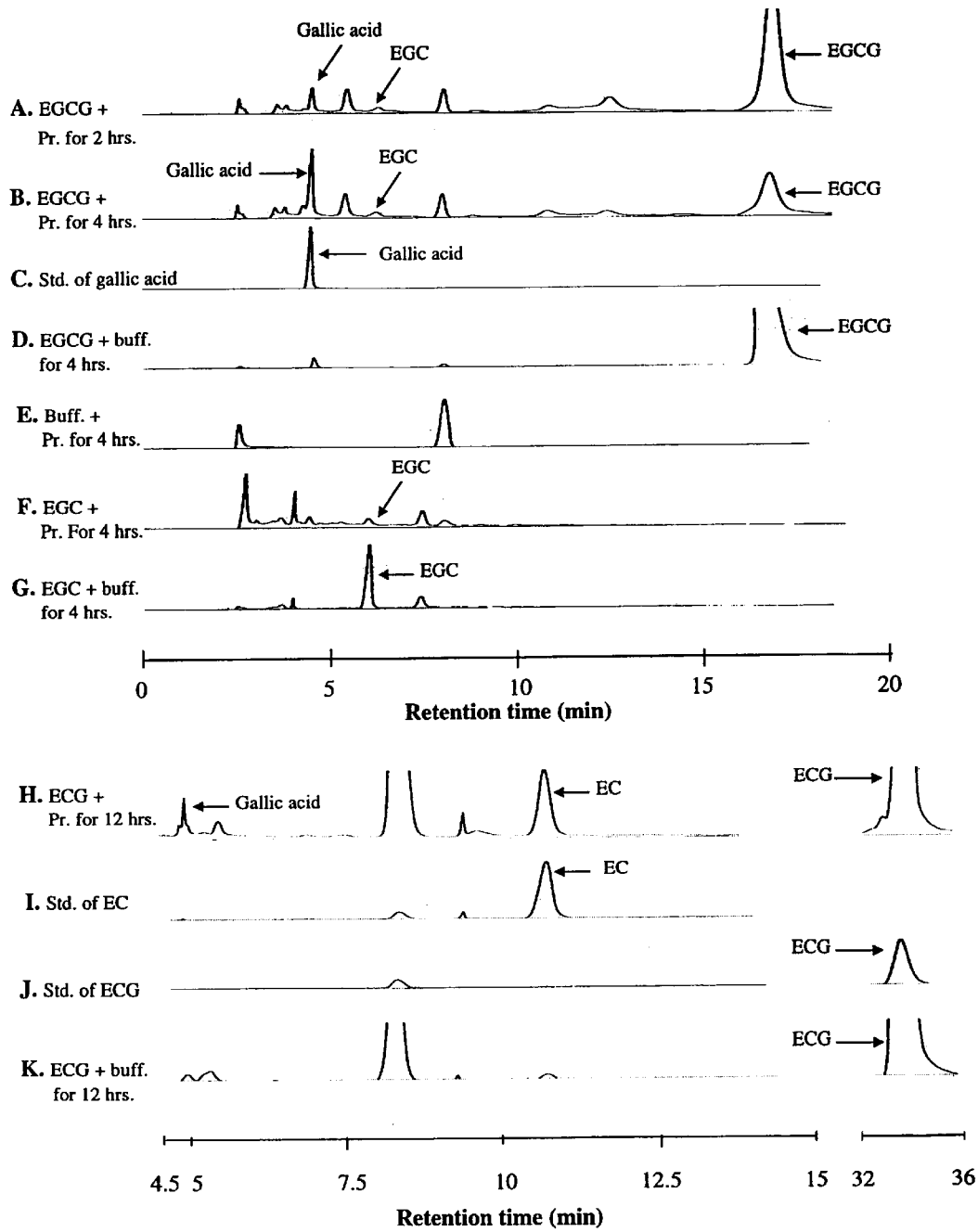
FIG. 2. HPLC chromatograms of proteasome proteolysis products of tea polyphenols. A purified 20S proteasome is incubated with a tea polyphenol, followed by HPLC analysis. Retention times of tea components are confirmed by using their standards (Std). Pr, the 20S proteasome; buff, buffer. L, Cleavage of EGCG by the purified 20S proteasome in time-dependent matter.
Figure 2:
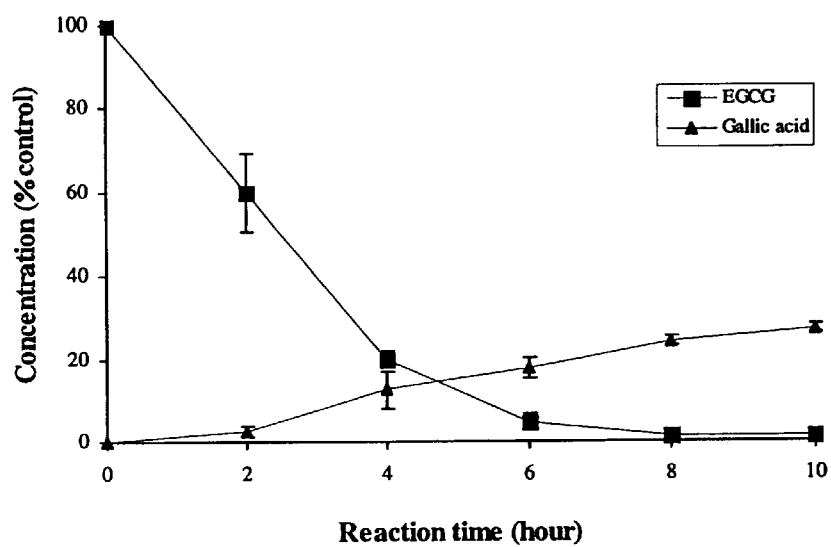

After a 2 h-incubation, associated with a 40% decrease in the level of EGCG, a gallic acid-like peak (retention time 4.78) is detected in the HPLC chromatogram, which corresponded to a concentration of <5% of EGCG (FIGS. 2A and L). Incubation of EGCG with the proteasome for 4 h results in disappearance of 80% EGCG, associated with an increase in the levels of the gallic acid-like peak which is equivalent to 13% of EGCG (FIGS. 2B and L). After a 6 h or longer incubation with the proteasome, >95% of EGCG disappears, while the level of the gallic acid-like product linearly increases to a level equivalent to 20–25% of EGCG (FIG. 2L). The gallic acid-like peak is not produced from EGCG in the absence of the proteasome (FIG. 2D). Incubation of EGCG with the 20S proteasome also results in appearance of an EGC-like product (retention time 6.62 min), although its level is low (FIGS. 2A and B vs. G). Thus, the produced EGC is further degraded by the proteasome. Indeed, purified EGC is degraded by the 20S proteasome (FIG. 2F). Similarly, incubation of ECG, another ester bond-containing polyphenol, with the purified proteasome results in gallic acid- and EC-like products (FIG. 2H). Again, a ~20% decrease in levels of ECG is found to be associated with 3–4% increase in the levels of both gallic acid-like and EC-like products. The unknown peak at retention time 8-min results from the mixture of buffer and purified proteasome (FIG. 2E). Targeting of the ester bond carbon in EGCG (or ECG) by the nucleophilic hydroxyl group of the proteasome results in formation of an EGCG (or ECG)-proteasome complex, followed by a slow cleavage of the complexed EGCG (or ECG) at the ester band and production of gallic acid and EGC (or EC).

EGCG, but not EGC, inhibits the 26S proteasome activity in a tumor cell extract and in living tumor cells. 10 μM EGCG inhibited ~70% of the proteasomal chymotrypsin-like activity in a Jurkat T cell extract while EGC at the same concentration has little effect (FIG. 3A). Addition of EGCG to the Jurkat cell extract also potently inhibits another proteasomal activity, the PGPH activity, but does not affect the proteasomal trypsin-like activity (FIG. 3A). To show that EGCG specifically inhibits the proteasome activity, other protease activities are examined. Purified calpain I enzyme is incubated with its fluorogenic peptide substrate, Suc-Leu-Tyr-AMC, in the absence or presence of EGCG or the specific calpain inhibitor calpeptin. Calpeptin, but not EGCG, is able to inhibit the activity of the purified calpain (FIG. 3B). Similarly, a caspase-3-like activity in Jurkat T cell extract is blocked by the specific caspase-3 inhibitor Ac-DEVD-CMK, but not EGCG (FIG. 3C). Thus, EGCG selectively inhibits the proteasomal chymothypsin (and PGPH) activity.

Figure 4:
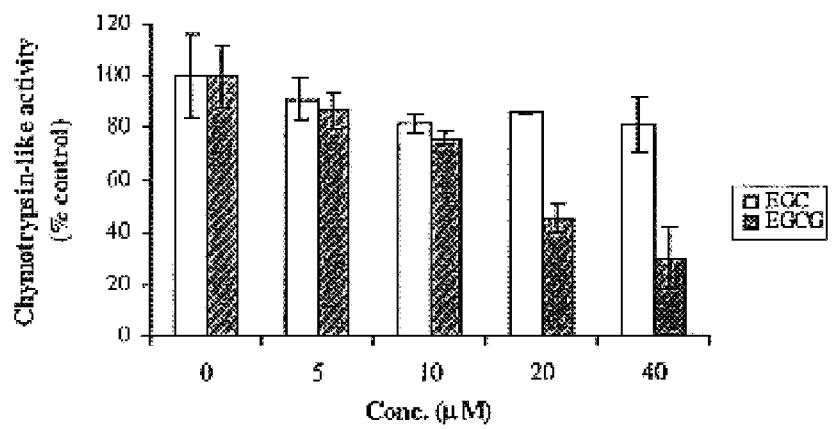
FIG. 4. Inhibition of the proteasome activity by EGCG, but not EGC, in intact Jurkat cells. Human Jurkat T cells are preincubated for 12 h with EGCG, EGC, β-lactone, or LLnL at the indicated concentrations, followed by an additional 2 h-incubation with fluorogenic substrates Suc-Leu-Leu-Val-Tyr-AMC for the chymotrypsin-like activity and Z-Gly-Gly-Arg-AMC for the trypsin-like activity. The medium is collected and the free AMC groups are measured as described in The Materials and Methods section of Example 1.
Figure 4:
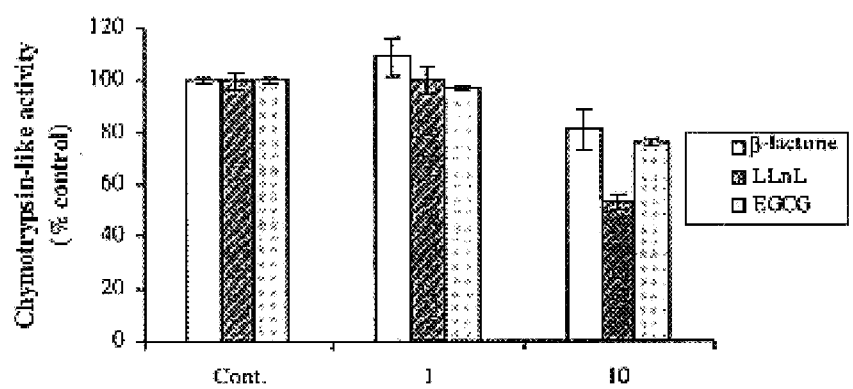
Figure 4:
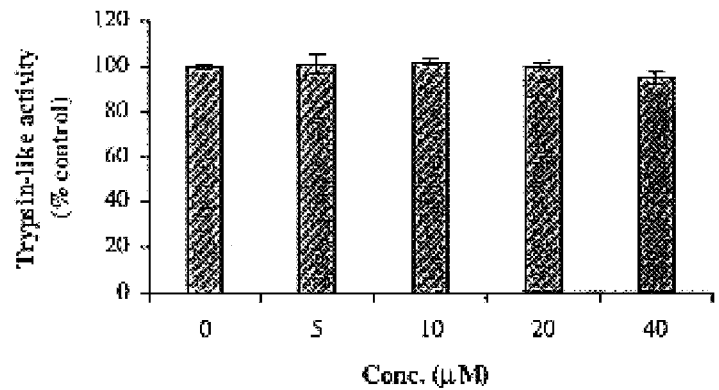

EGCG significantly inhibits the proteasome chymotrypsin-like activity in living Jurkat cells in a concentration-dependent manner ($IC_{50}$ 18 μM), whereas EGC has much less effect (FIG. 4A). Similar to the specific proteasome inhibitor β-lactone and the proteasome inhibitor LLnL, the concentration of EGCG needed to inhibit the proteasome activity in living cells is higher than that for the purified proteasome (compare FIG. 4 vs. 1). β-lactone, LLnL and EGCG at 10 μM inhibited 20%, 40%, and 24% of chymotrypsin-like activity, respectively (FIG. 4B). EGCG also inhibits the chymotrypsin-like activity in living breast (MCF7) and prostate (PC-3) cancer cells. However, EGCG does not inhibit the trypsin-like activity in living Jurkat T cells (FIG. 4C). Therefore, EGCG, but not EGC, at low concentrations selectively inhibits the chymotrypsin-like activity of purified 20S proteasome, 26S proteasome of tumor cell extracts, and 26S proteasome of living tumor cells.

To demonstrate the direct consequences of inhibiting the proteasome activity by EGCG, Jurkat T cells are treated with EGCG or EGC, followed by measurement of levels of the cyclin-dependent kinase inhibitor p27$^{Kip1}$ and inhibitor of transcription factor NF-κB (IκB), two target proteins of the proteasome (Pagano et al., (1995) *Science* 269(5224), 682–5; Verma et al., (1995) *Genes Dev* 9(22), 2723–35). Treatment of intact Jurkat T cells with 1 or 10 μM of ECGC for 12 h greatly increases the levels of p27, but EGC at the same concentrations does not (FIG. 5A). The EGCG treatment also increases the levels of IκB-α and some ubiquitinated proteins (FIGS. 5B and C). p27 and IκB-α protein levels in prostate cancer cell line LNCaP increase upon treatment with EGCG. Treatment of EGCG at 1 or 10 μM for 12 h accumulated both p27 and IκB protein expression (FIG. 5D).

Figure 5:
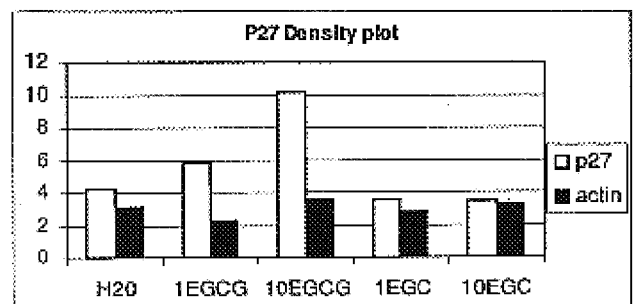
FIG. 5. Western blot analysis. A, Jurkat T cells are treated with 1 or 10 μM of EGCG or EGC for 12 h, or B, C, 25 μM of EGCG for various times, followed by Western blot assay using specific antibodies to p27, IκB-α, ubiquitin or actin, as indicated. MWs of IκB-α and actin are 40 and 43 kDa, respectively. The band of 56 kDa, indicated by an arrow in (B), is an ubiquitinated or phosphorylated form of IκB-α. The bands indicated in (C) are ubiquitin-containing proteins. D, LNCaP cells are treated with 1 or 10 μM of EGCG for 12 h. Western bot is performed as described above. E, F, Jurkat T cells are pretreated with 10 μg/ml cycloheximide for 2 hr, followed by co-incubation with 1 or 10 μM of EGCG for 8 or 12 hr as indicated. The p70 is a putative ubiquitinated p27-containing complex (An et al., 1998, $Cell\ Death\ Differ$ 5: 1062–75).
Figure 5:
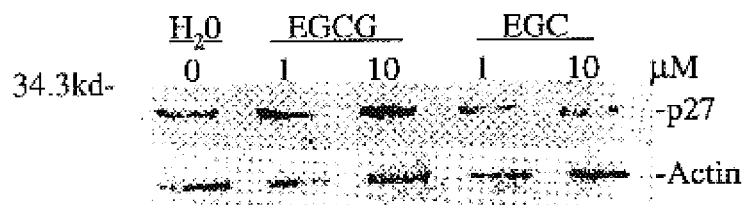
Figure 5:
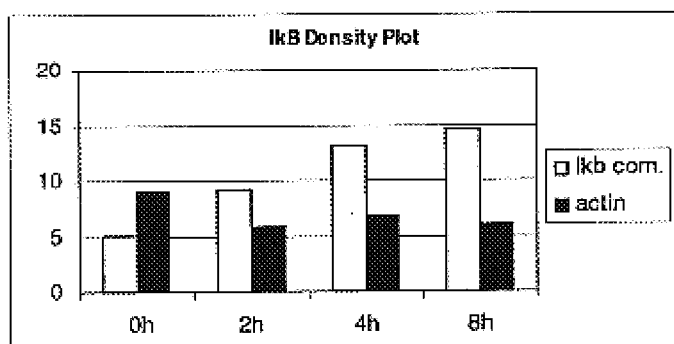
Figure 5:
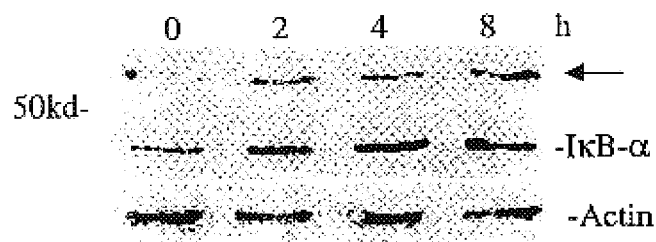
Figure 5:
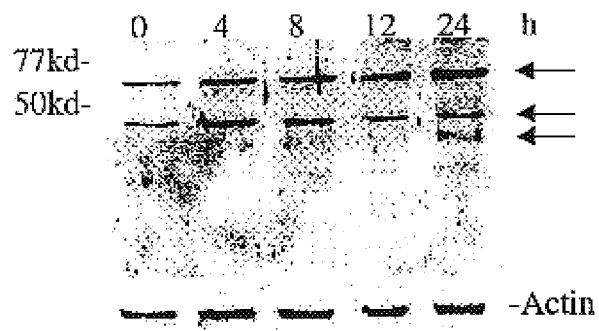
Figure 5:
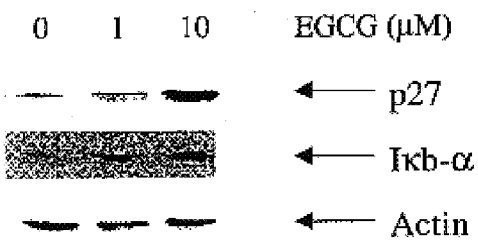
Figure 5:
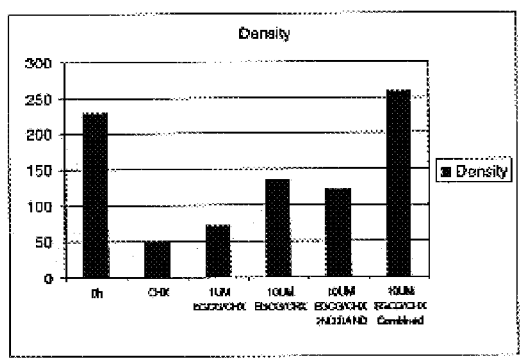
Figure 5:
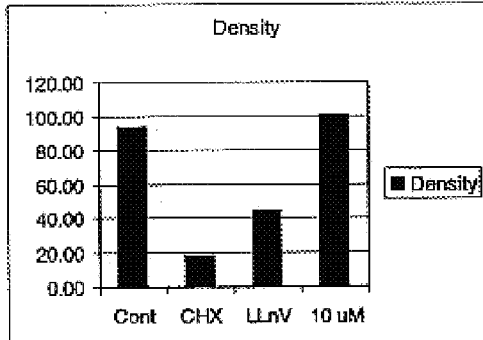
Figure 5:
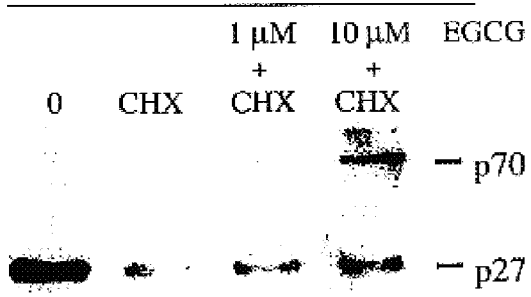
Figure 5:
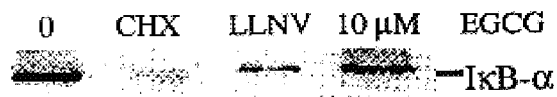

To show inhibition of the proteasome-mediated degradation of p27 and IκB by EGCG, human Jurkat T cells are pretreated with cycloheximide (a protein synthesis inhibitor) and then co-treated with EGCG. The cycloheximide treatment significantly decreases levels of both p27 and IκB protein (FIGS. 5E and F, lanes 2 vs. 1). When the cycloheximide-pretreated cells are co-incubated with EGCG at 10 μM, levels of p27 protein are dramatically increased (FIG. 5E, lanes 4 vs. 2). Co-incubation of cycloheximide and EGCG also increase the level of a p70 (FIG. 5E, lanes 4 vs. 2), a putative ubiquitinated p27-containing protein (7). Co-incubation of the cycloheximide-pretreated cells with EGCG at 10 μM also increases levels of IκB protein (FIG. 5F, lanes 4 vs. 2), and the EGCG-mediated induction of IκB expression is even greater than that of the proteasome inhibitor LLnV at the same concentraiton (FIG. 5F, lanes 4 vs. 3). Therefore, inhibition of the proteasomal chymotrypsin-like activity in living tumor cells (FIG. 4A) correlates well with accumulation of p27, IκB-α and some ubiquitinated proteins (FIG. 5).

Because EGCG-accumulated p27 is functional, cell growth is arrested in $G_1$ (13). 24 h treatment of Jurkat T cells with EGCG at 10 μM increases their G1 population by 10%. Exposure of LNCaP prostate cancer cells to 10 μM EGCG for 36 h increases $G_1$ population by ~25% (FIG. 6A).

Proteasome inhibitors selectively accumulate p27 protein and induce apoptosis in tumor and transformed but not normal human cells. EGCG selectively targets tumor or transformed cells but not normal cells. Thus, normal human WI-38 cells and SV-40-transformed WI-38 cells (VA-13) are treated with 10 μM of EGCG, followed by measurement of p27 levels and cell cycle distribution. Treatment of VA-13 cells with EGCG increases $G_1$ population by 21% at 12 h and by 33% at 36 h (FIG. 6B). In contrast, a 12 h treatment of WI-38 cells does not block their cell cycle progression: a 22% decrease in $G_1$ population is observed, associated with a 16% increase in S and a 6% increase in $G_2$/M population (FIG. 6B). Only the 36 h treatment with EGCG increases the $G_1$ population of WI-38 cells by 22% (FIG. 6B). Thus, EGCG selectively inhibits the proteasome activity and induces cell cycle arrest in tumor and transformed cells, but not normal human fibroblasts.

Figure 6:
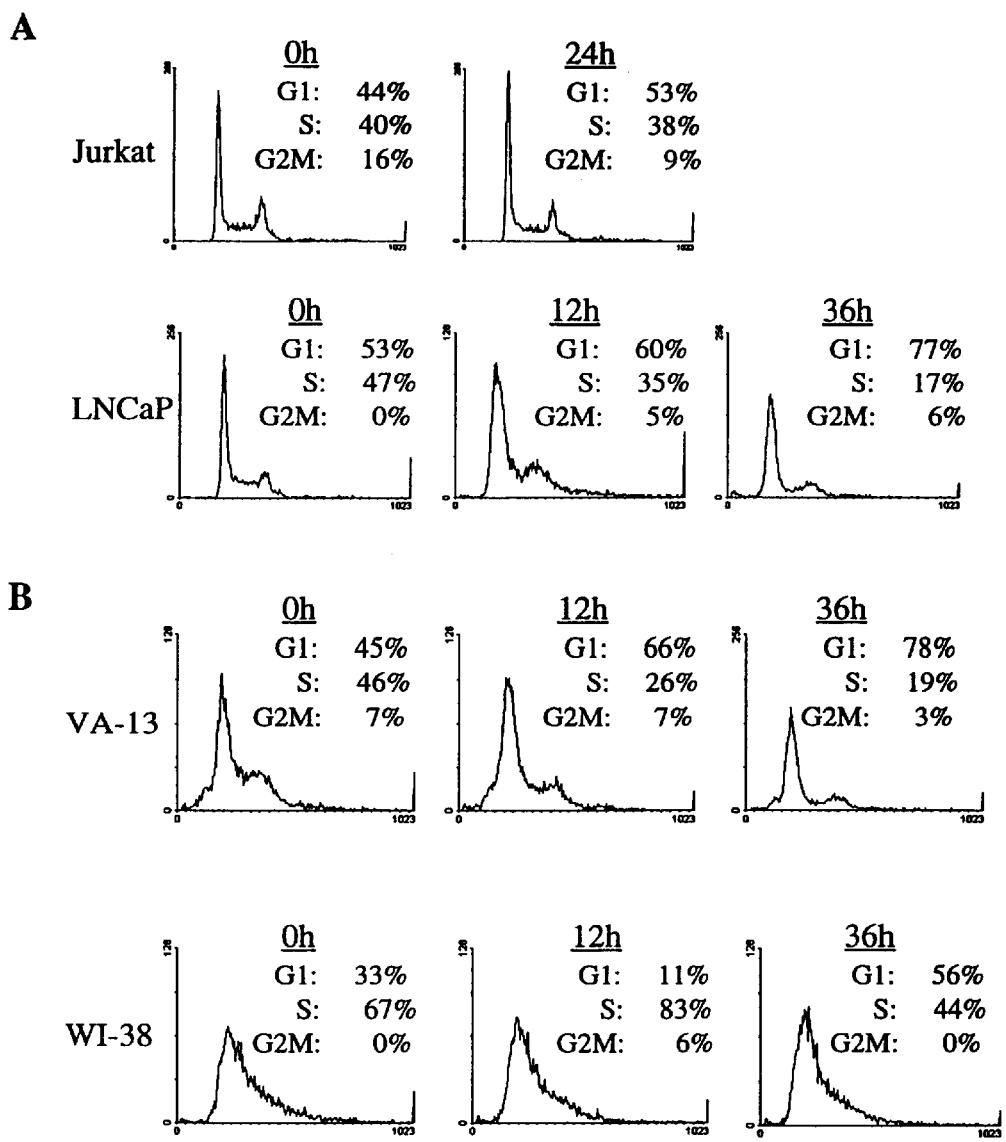
FIG. 6. Cell cycle analysis. Asynchronous Jurkat, LNCaP, WI-38, and VA-13 cells are treated with 10 μM EGCG and harvested at the time points indicated. Cells are prepared and analyzed by flow cytometry as described in the The Materials and Methods section of Example 1. Growth arrest is determined by the increase in the percentage of $G_1$ population.

It is disclosed herein that proteasome chymotrypsin-like activity by ester bond-containing tea polyphenols is a novel mechanism for the cancer preventative effects of tea. Inhibition of the chymotrypsin-like, but not trypsin-like, activity by a specific proteasome inhibitor is sufficient to induce tumor cell apoptosis and growth arrests. EGCG, the most abundant component of green (51.5%) tea extracts and of black (19.7%) tea extracts (see the Materials and Methods section of Example 1), is a potent inhibitor of the proteasome chymotrypsin-like activity both in vitro and in vivo (FIGS. 1, 3, 4, 5). Treatment of Jurkat T and LNCaP cells with EGCG accumulated p27, IκB-α, and some ubiquitin-containing proteins (FIG. 5), which is associated with $G_1$ arrest (FIG. 6). Therefore, disclosure herein demonstrates the essential roles of p27 and IκB in inhibiting cell proliferation, and shows that EGCG targets the proteasome in tumor cells.

Figure 3:
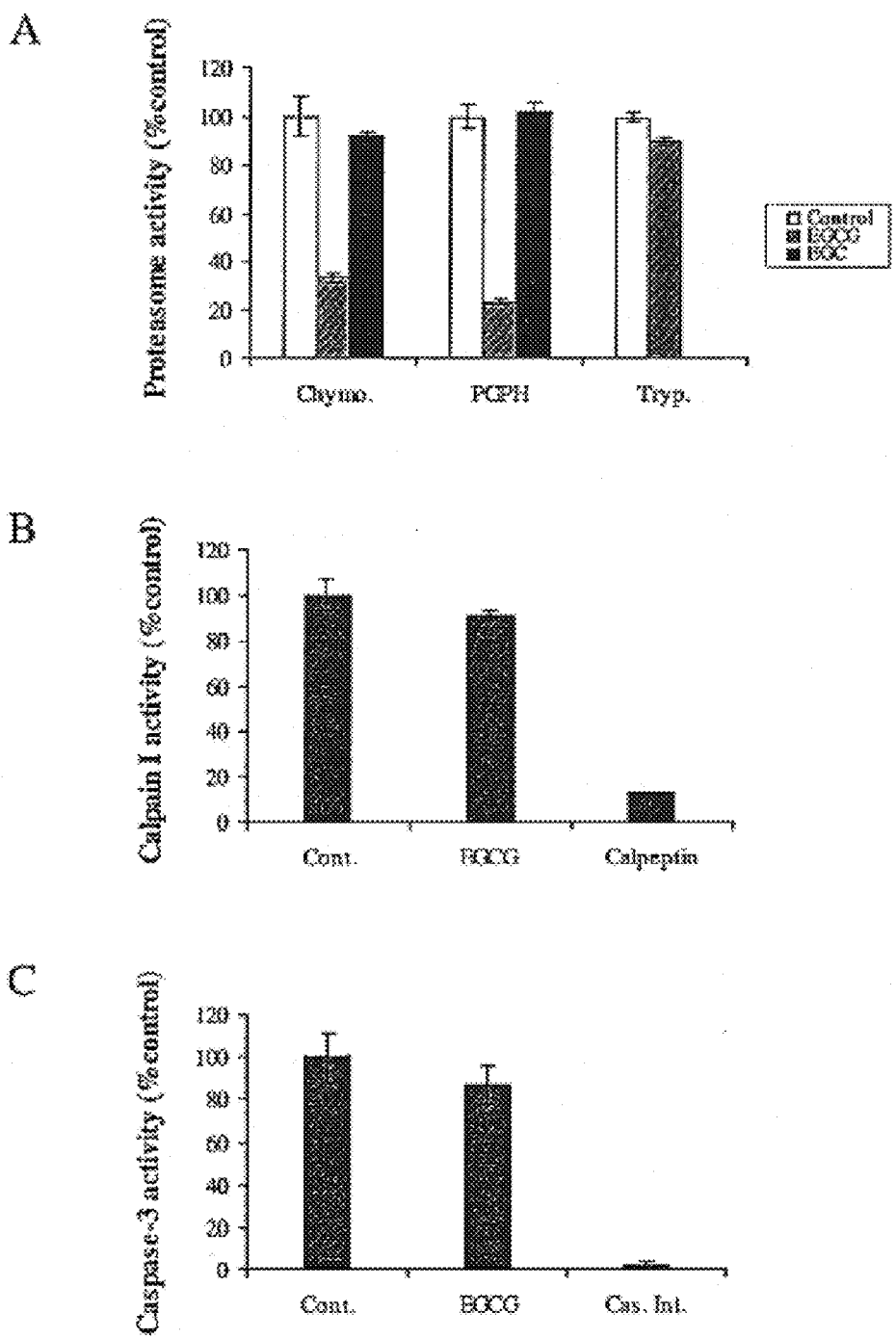
FIG. 3. Specificity for inhibition of the proteasome activity by EGCG, but not EGC, in a Jurkat cell extract. Protein extracts for the proteasomal chymotrypsin-like, PGPH, trypsin-like activity, and caspase-3 activity, and purified calpain I are incubated for 90 min with various fluorogenic substrates in the absence or presence of EGCG (10 μM), EGC (10 μM), calpeptin (1 μM) or Ac-DEVD-CHO (10 μM), as indicated, followed by measurement of free AMC groups as described in The Materials and Methods section of Example 1 (P<0.05).

A low micromolar range of EGCG was found to be effective for inhibiting the proteasome activity in tumor cell extracts and living tumor cells (FIGS. 3–5). This result was comparable to previous studies in which low micromolar levels of EGCG or other catechins are found in plasma and saliva of human volunteers (Yang, C. S. (1999) *Nutrition* 15(11–12), 946–9; Yang et al. (1999) *Cancer Epidemiol Biomarkers Prev* 8(1), 83–89), and in mice that had been fed with tea (Yang et al. (1999) *Cancer Epidemiol Biomarkers Prev* 8(1), 83–89). Therefore, our results show that EGCG at the physiological level can inhibit the proteasome activity in living cancer cells.

In HPLC analysis for cleavage products of EGCG by the proteasome, even though the gallic acid-like product linearly increased with increasing reaction time, the level of appearance of gallic acid-like peak was much lower than that of disappearance of EGCG (FIG. 2L). This is because EGCG remains bound to the proteasome, and release of gallic acid-like product is slow.

From results diclosed herein it can be inferred that the two nucleophilic electrons located on the N-terminal threonine hydroxyl group of the proteasome subunit X attack the ester bond carbon of EGCG (or ECG). Subsequently, a reversible EGCG (or ECG)-proteasome complex is generated, thereby inactivating the proteasome. This complex slowly disassociates to form free EGC (or EC) and an intermediate complex of gallic acid and the proteasome. This complex is susceptible to another nucleophilic attack by a water molecule, resulting in release of gallic acid from the proteasome.

In summary, in this example it is shown that tea polyphenols containing ester bonds are potent proteasome inhibitors, are useful in cancer prevention, and also in a clinical therapy in combination with current anticancer drugs.

EXAMPLE 2

Proteasome Inhibition by Tannic acid

Figure 7:
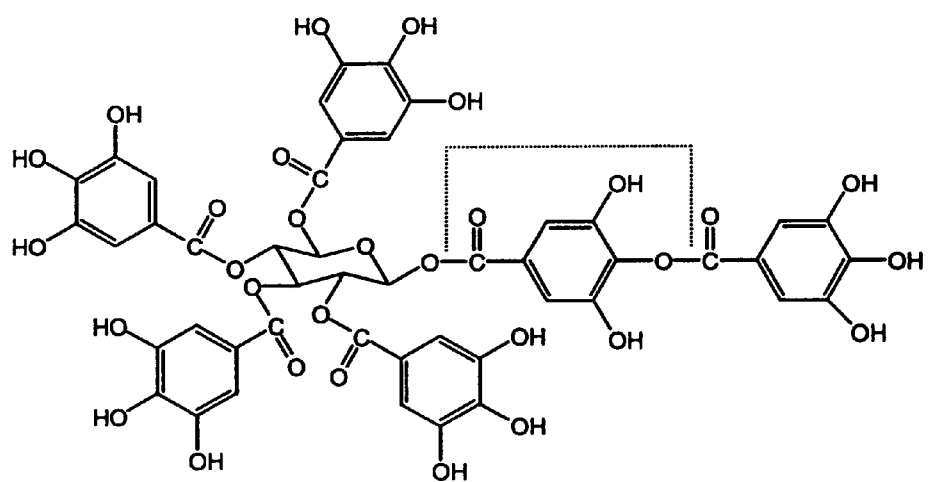
FIG. 7. Shows the structure of tannic acid.
Figure 8:
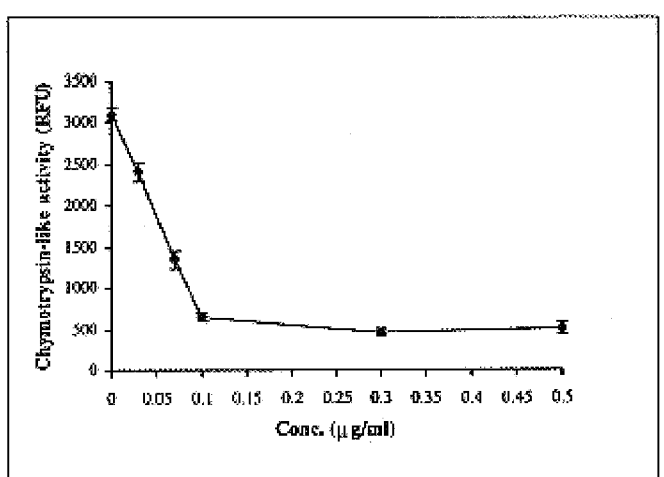
FIG. 8. Inhibition of the purified 20S proteasome activity in vitro by tannic acid. A). Inhibition of the chymotrypsin-like activity of the proteasome by tannic acid is concentration-dependent. Initially, 0.5 μg of purified 20S proteasome is incubated with 20 μM of a fluorogenic peptide substrate, Suc-Leu-Leu-Val-Tyr-AMC, for 30 min at 37° C. in 100 μl of assay buffer (20 mM Tris-HCl, pH 8.0) with various concentrations of tannic acid. After incubation, the reaction mixture is diluted to 200 μl with the assay buffer, followed by measurement of the hydrolyzed 7-amido-4-methyl-coumarin (AMC) groups using a fluorometer with an excitation filter of 380 nm and an emission filter of 460 nm. B). The chymotrypsin-like activity of the proteasome is inhibited by tannic acid but not glucose. Tannic acid (0.3 μg/ml) and Glucose (180 μg/ml) are used in the proteasome activity assay as described above. C). Tannic acid does not inhibit calpain activity. Purified calpain I (3 μg) protein is incubated with 40 μM of a fluorogenic peptide substrate, Suc-Leu-Tyr-AMC, for 30 min at 37° C. in 100 μl of assay buffer (50 mM Tris-HCl, pH 7.5, containing 50 mM NaCl, 1 mM EDTA, 1 mM EGTA, 5 mM β-Mercaptoethanol, 5 mM $CaCl_2$, and 0.1% CHAPS) in the absence (control) or presence of 5 μg/ml of tannic acid or 0.18 μg/ml of calpeptin (calpain inhibitor).
Figure 8:
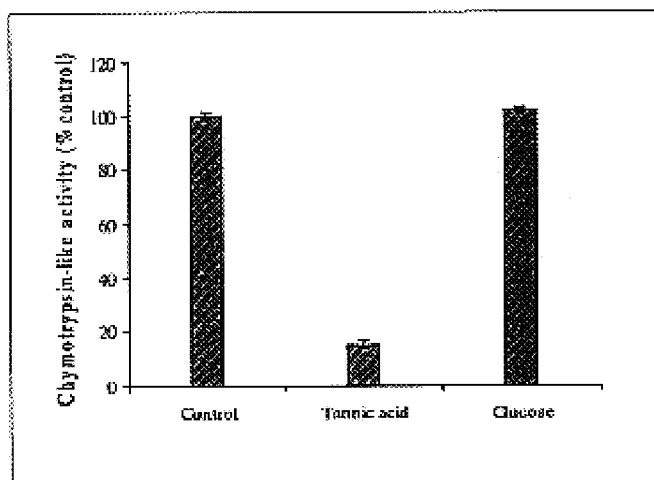
Figure 8:
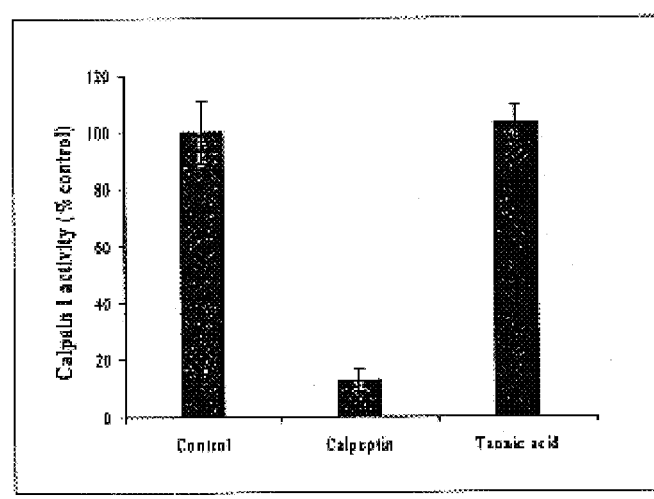
Figure 9:
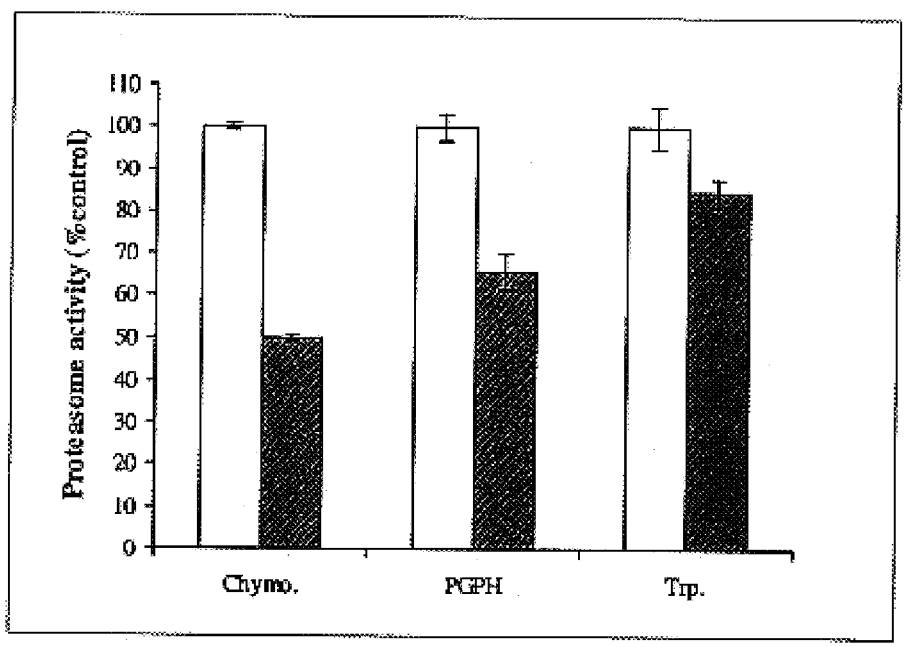
FIG. 9. Inhibition of the proteasome activity by tannic acid using a cell free extract. A). The whole cell extract (6.0 μg) from Jurkat T cells is incubated for 90 min at 37° C. with 20 μM of a fluorogenic peptide substrate, Suc-Leu-Leu-Val-Tyr-AMC for the chymotrypsin-like activity, Z-Leu-Leu-Glu-AMC for peptidyl-glutamyl peptide-hydrolyzing (PGPH) activity, and Z-Gly-Gly-Arg-AMC for the trypsin-like activity, in 100 μl of the assay buffer with (filled bars) or without (empty bars) 1 μg/ml of tannic acid. The hydrolyzed AMCs are quantified as described in FIG. 2. B). Dose-dependent inhibition of the chymotrypsin-like activity by tannic acid. Experiment is performed as described in FIG. 9A.
Figure 9:
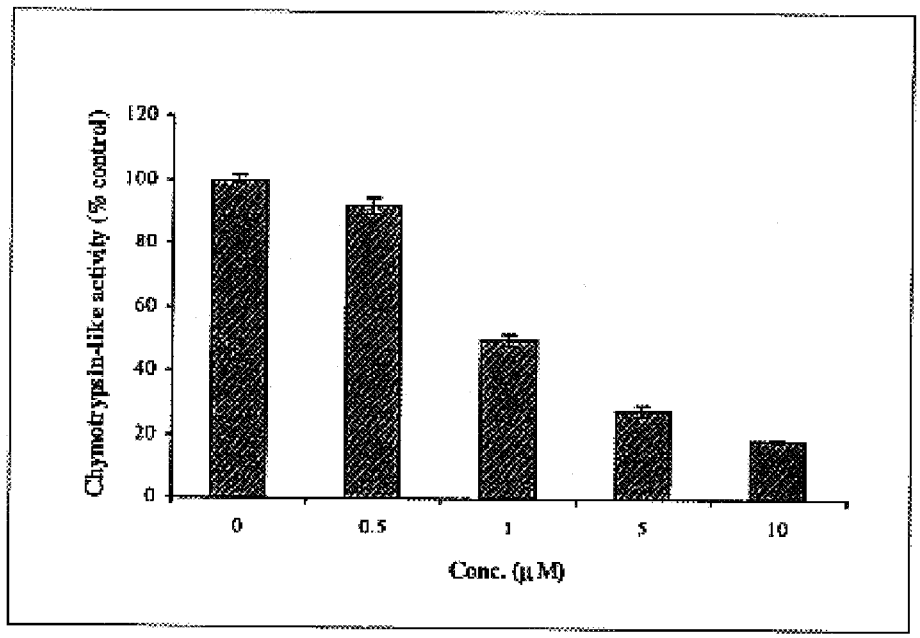
Figure 10:
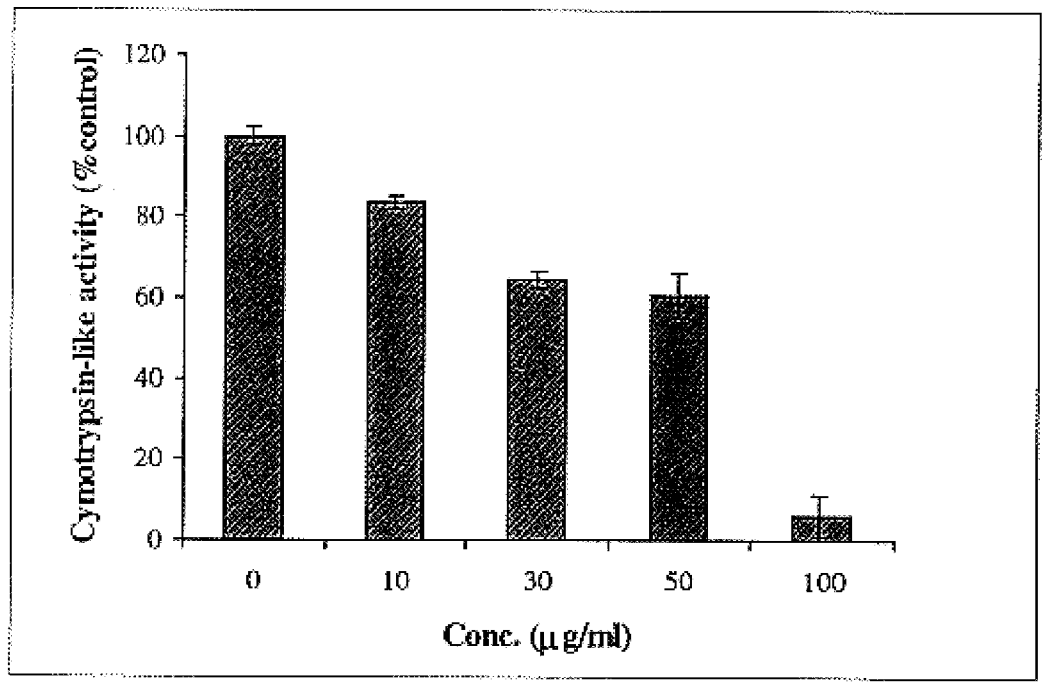
FIG. 10. Inhibition of the chymotrypsin-like activity by tannic acid in intact Jurkat T cells. Intact Jurkat T cells ($1\times10^5$ cells/ml/well) are cultured in 24-well plates. These cells are first incubated for 12 h with various concentrations of tannic acid as indicated, followed by an additional 2 h-incubation with a fluorogenic peptide substrate, Suc-Leu-Leu-Val-Tyr-AMC for the chymotrypsin-like activity. Then, cell medium (200 μl per sample) is collected and used for measurement of free AMCs.
Figure 11:
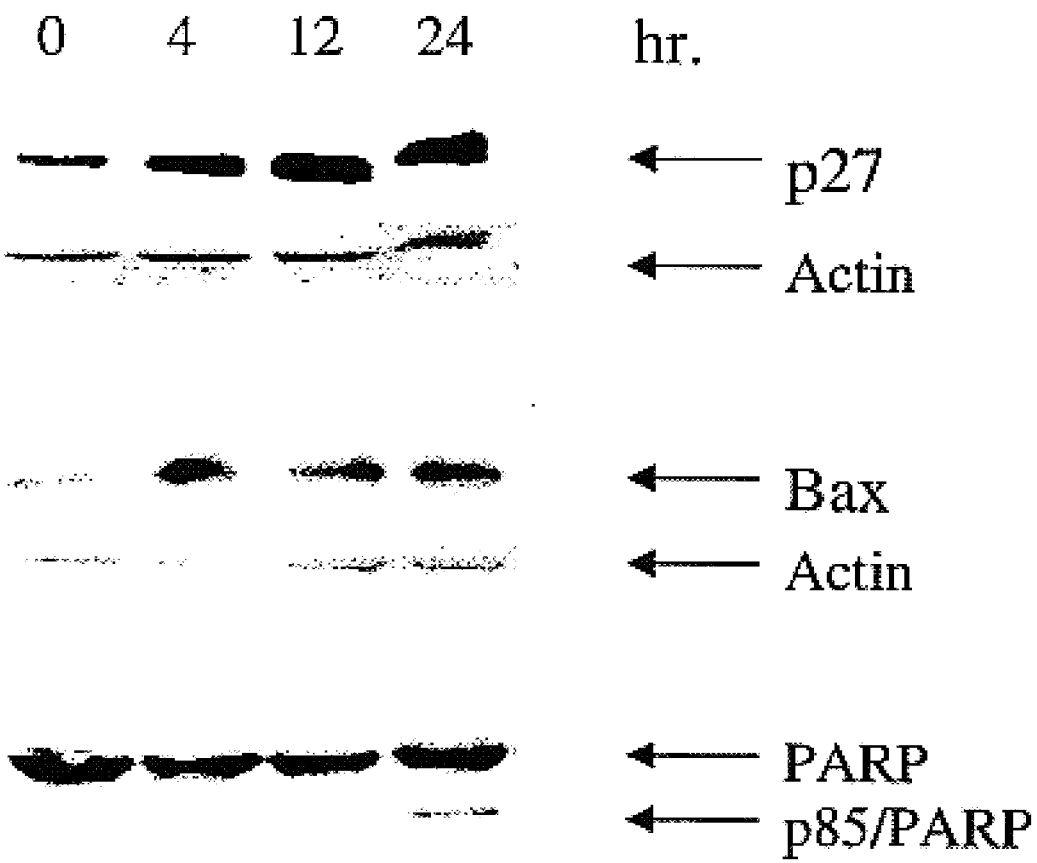
FIG. 11. Western blot assay. Western blot assay is performed using specific antibodies to $p27^{Kip}$, Bax, poly(ADP-ribose) polymerase (PARP), or actin. Jurkat T cells are treated with 50 μg/ml of tannic acid for 4, 12 or 24 h. Cells are harvested and lysated using the whole lysis buffer (50 mM Tris-HCl, pH 8.0, 5 mM EDTA, 150 mM NaCl, 0.5% NP-40, 0.5 mM PMSF, and 0.5 mM DTT). Cell lysates (70 μg) are separated on a sodium dodecyl sulfate-polyacrylamide gel electrophoresis (SDS-PAGE), followed by Western blot analysis.
Figure 12:
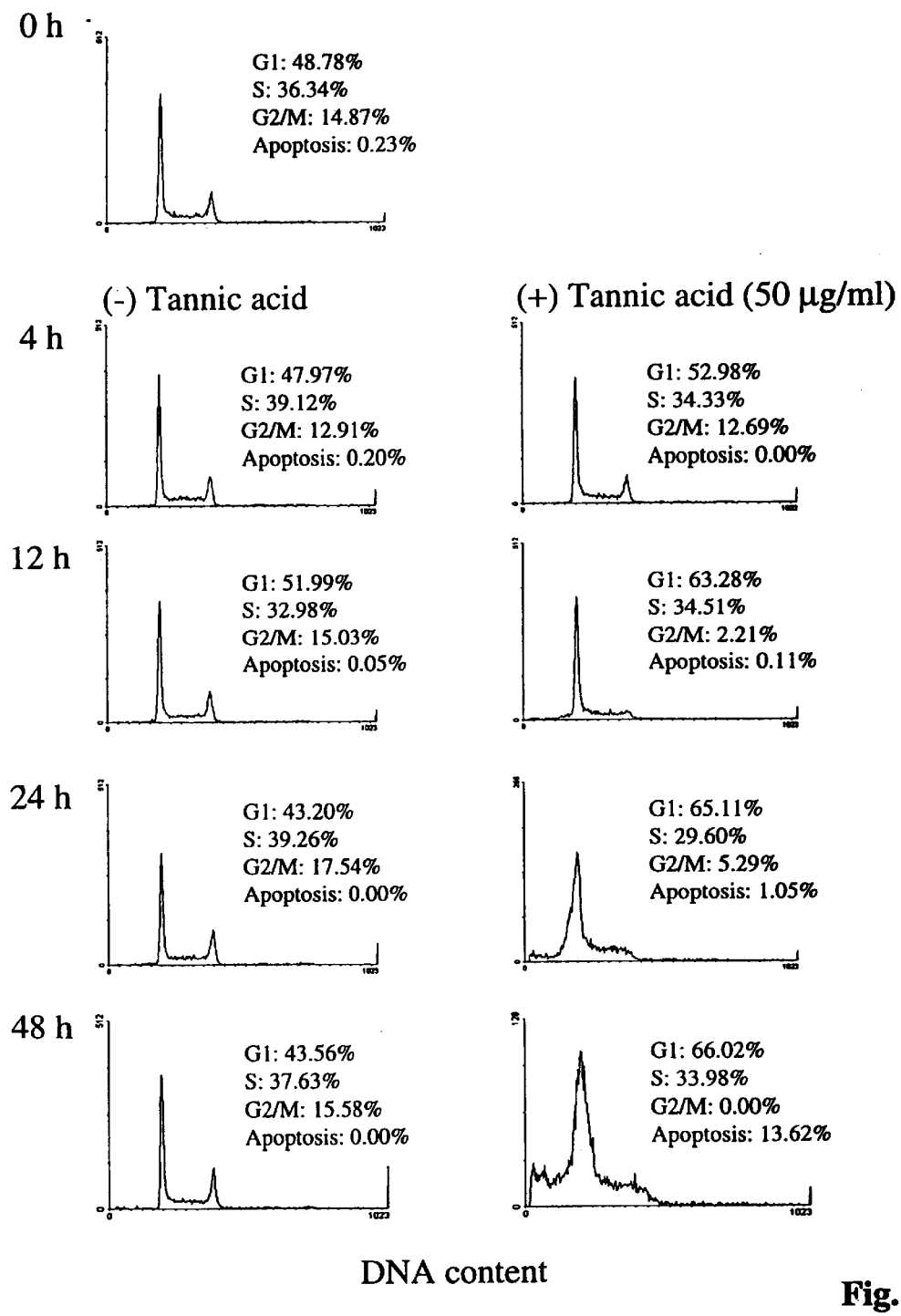
FIG. 12. Tannic acid treatment induces $G_1$ arrest and apoptosis. Jurkat T cells are treated with either 50 μg/ml of tannic acid or buffer (-) for up to 48 h. The harvested cells are fixed, resuspended in 1 ml of PBS containing 50 μg/ml of propidium iodide (PI), 100 U/ml of RNase A, and 1 mg/ml of glucose, and analyzed by flow cytometry. Percentages of cells containing $G_1$ S, $G_2$ and M DNA content are indicated. Percentages of the apoptotic cell population containing sub-$G_1$ DNA content is also indicated. Note: tannic acid treatment results in ~23% increase in $G_1$ and ~14% increase in apoptotic cell populations.

Using methods essentially as disclosed in example 1, it is shown in this example that tannic acid, which also contains esters, inhibits proteasome activity with similar specificity and mechanism as that disclosed above for tea polyphenol esters. Thus, the structure of tannic acid is shown in FIG. 7. Using methods described in the legend to FIG. 8, it is shown that purified 20S proteasome activity is inhibited in vitro by tannic acid. Furthermore, by methods disclosed in the legend, FIG. 9 shows that proteasome activity of cell free extracts of Jurkat T cells is also inhibited by tannic acid in a dose-dependent manner. The mechanism of tannic acid-mediated preteasome inhibition is further defined by the methods disclosed in the legend to FIG. 10, which shows inhibition of specifically chymotrypsin-like proteasome activity by tannic acid in intact Jurkat T cells. FIG. 11 discloses Western blot assays of lysates of Jurkat T cells treated with tannic acid, and show induction of p27$^{Kip}$ and Bax by tannic acid treatment. Finally, it is shown in FIG. 12 by flow cytometry that tannic acid treatment induces $G_1$ arrest and apoptosis.

Thus, this example parallels example 1 in demonstrating a similar mechanism of proteasome inhibition by tannic acid and tea polyphenol esters.

EXAMPLE 3

Ester-Bond Containing Inhibitors of Proteasome Activity

Figure 13A:
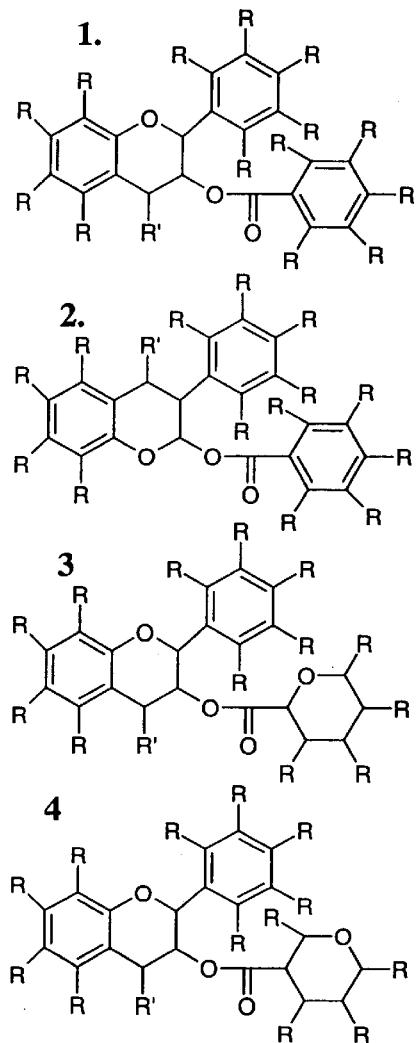
FIGS. 13A–C shows polyphenol esters of the present invention, and preferred substituents, that inhibit proteasome activity.
Figure 13A:
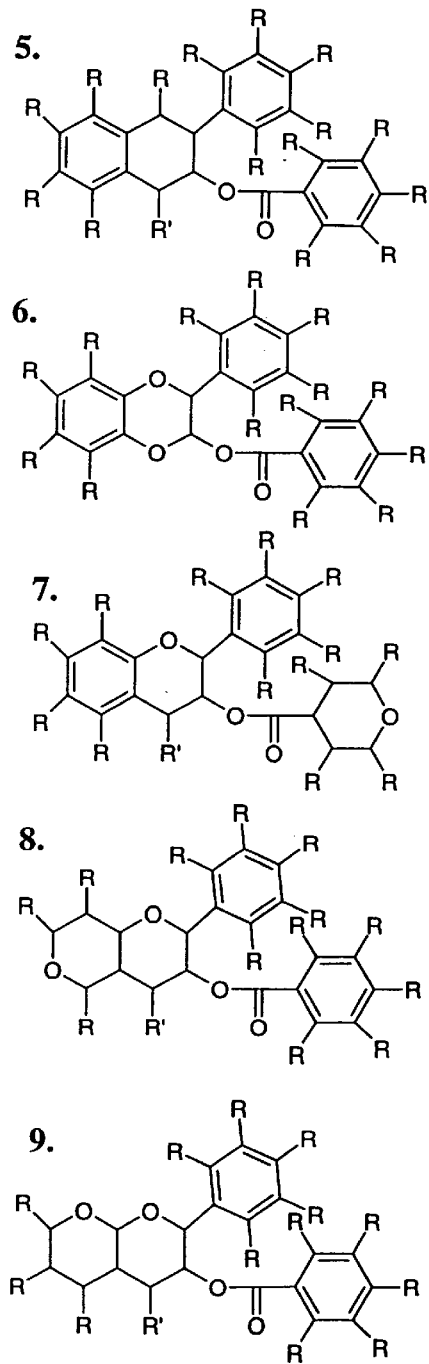
Figure 13B:
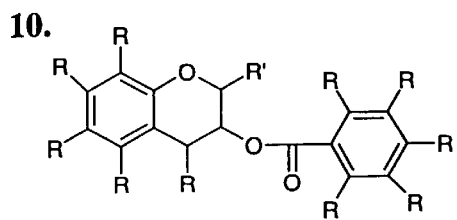
Figure 13B:
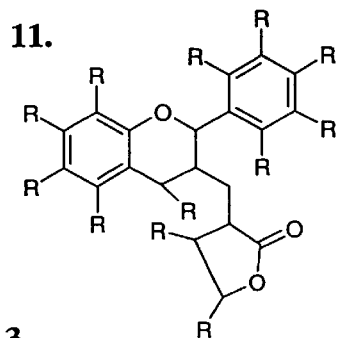
Figure 13B:
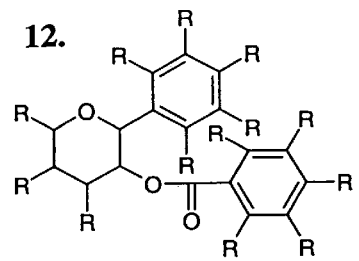
Figure 13B:
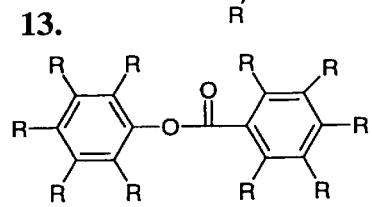
Figure 13B:
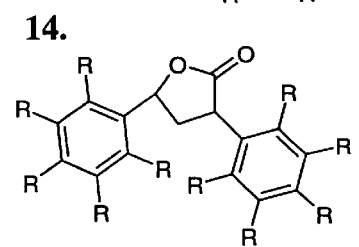
Figure 13B:
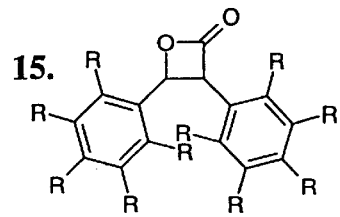
Figure 13B:
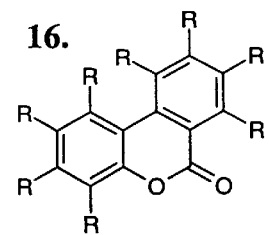
Figure 13B:
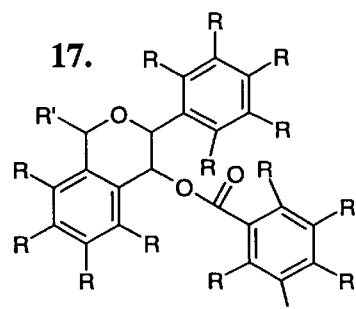
Figure 13B:
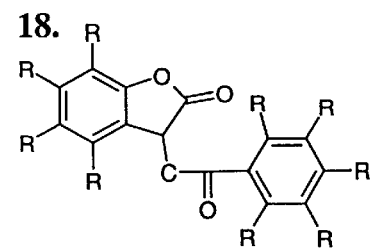
Figure 13B:
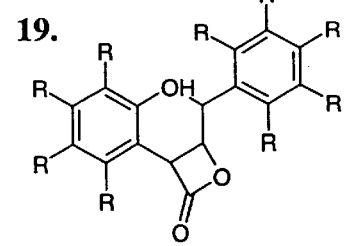
Figure 13C:
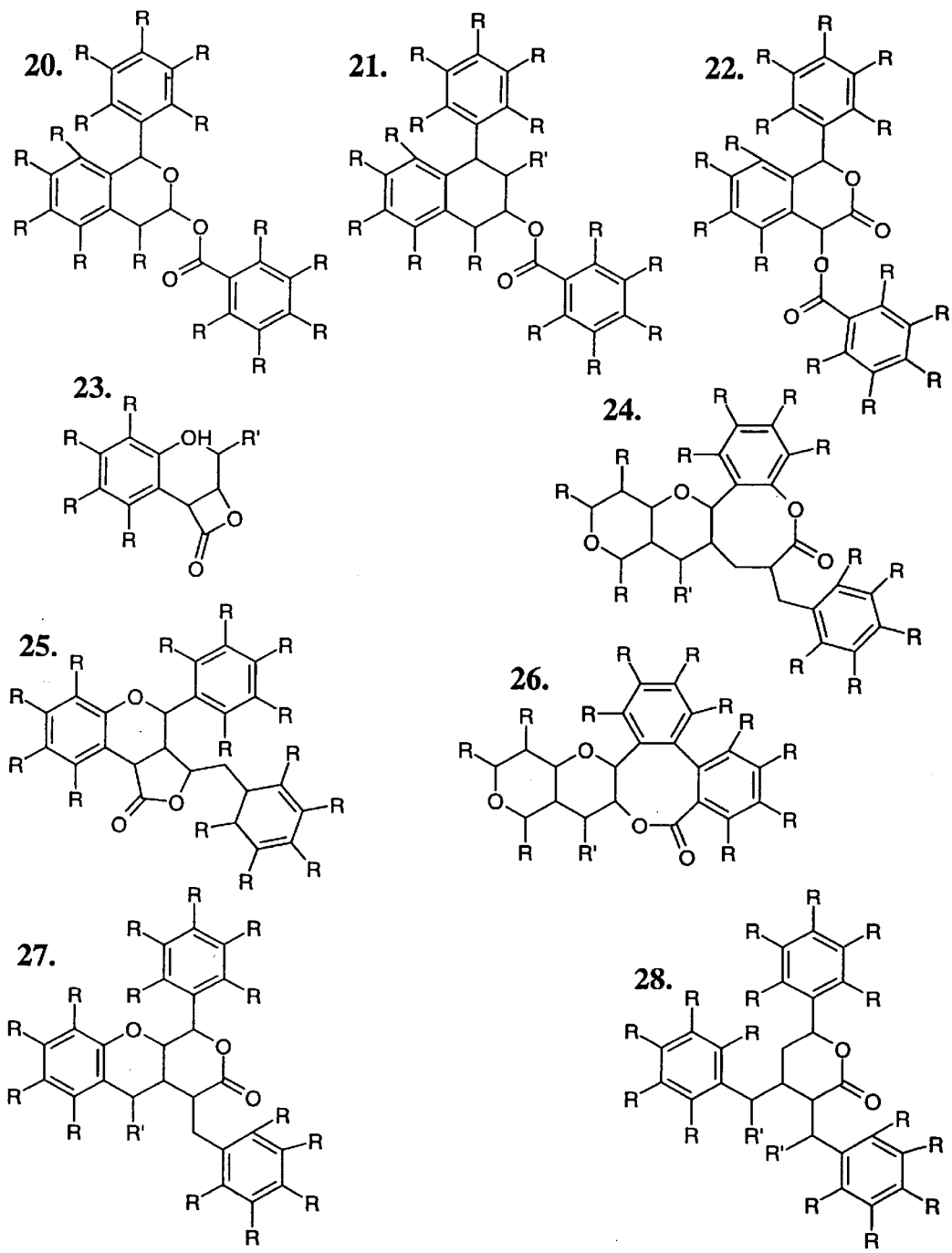

The compounds, shown in FIGS. 13A–C and numbered 1–28, presumptively inhibit the proteasome due to the presence of the ester-bond and the high number of hydrogen bonding atoms that are necessary for binding. These structures are designed based on the physiological moieties and parameters of ester-bond containing tea polyphenols and tannic acids. The possibilities of R and R' groups listed below can therefore be added in any order or combination to yield active compounds:

| R Groups | R' Groups |
|---|---|
| —H | =O |
| —OH | —H |
| —NH | —OH |
| —OCH$_3$ | —NH$_2$ |
| —CH$_2$OH | OCH$_3$ |
| —CH$_2$NH$_2$ | CH$_2$OH |
| -GALLATE | CH$_2$NH$_2$ |
|  | GALLATE |

EXAMPLE 4

Theaflavins as Inhibitors of Proteasome Activity

Theaflavins, black tea components, are generally produced through fermentation of natural leaves. The IC$_{50}$ value of black tea extract in vitro was 0.3 µg/ml. Based on the foregoing disclosure, ester-bond containing theaflavins such theaflavin 3-gallate, theaflavin 3'-gallate, and theaflavin 3,3'-gallate are also protesome inhibitors. Such compounds are disclosed in FIG. 14.

Theasinensin A (FIG. 14), a minor component of green tea extract is a dimeric flavan-3-ol gallate (a bisflavanol), which is a condensed form of EGCG. This component is presumptively a proteasome inhibitor, and its potency may be higher than EGCG due to the increasing intramolecular hydrogen bonding possibilities between theasinensin A and the proteasome.

Figure 14:
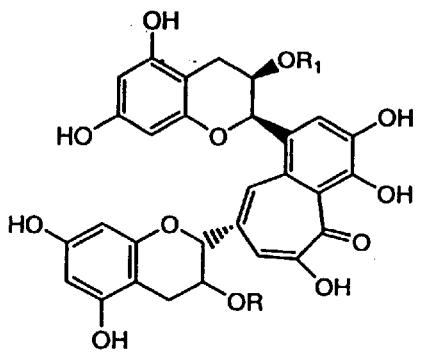
FIG. 14 shows theaflavin inhibitors of proteasome activity.
Figure 14:
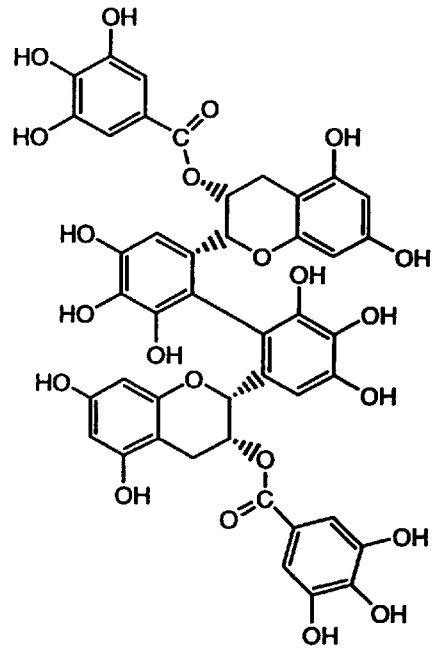
Figure 14:
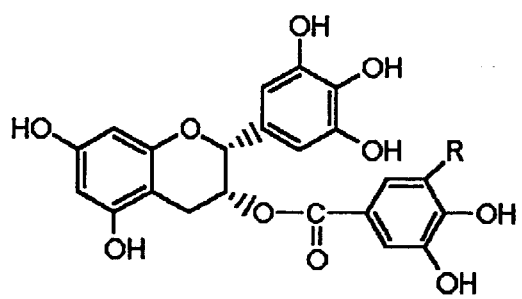

Analogs of EGCG and ECG with OCH$_3$ at 3' position are also disclosed herein as proteasome inhibitors (see FIG. 14).

EXAMPLE 5

Structural Requirements for Proteasome Inhibition

Figure 15A:
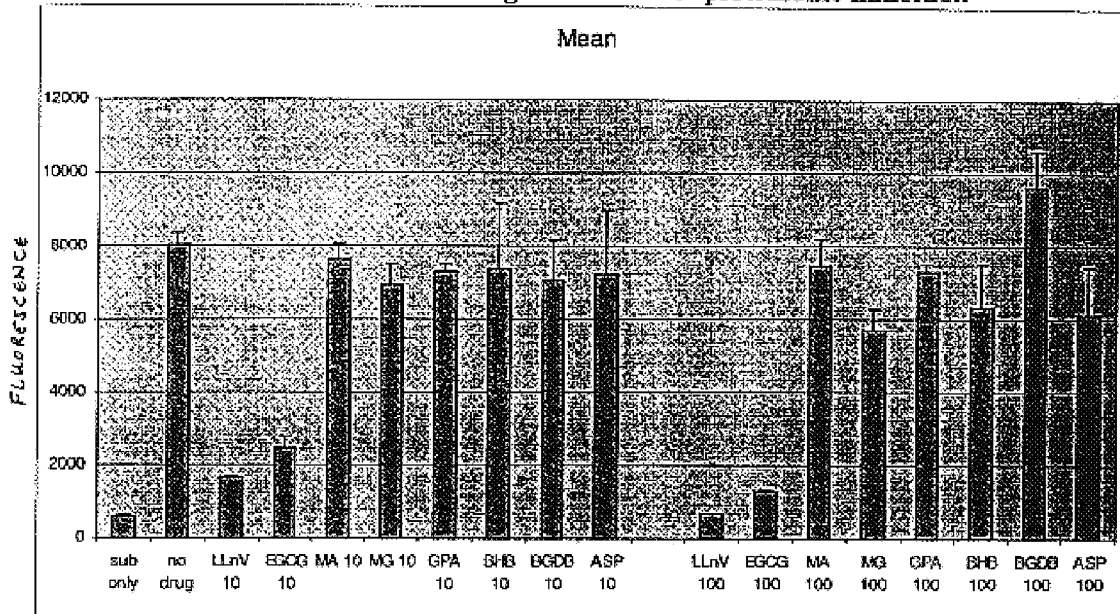
FIG. 15 shows ester-bond containing molecules and their proteasome inhibitory activities.
Figure 15A:
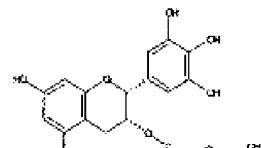
Figure 15A:
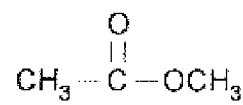
Figure 15A:
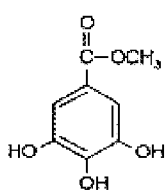
Figure 15A:
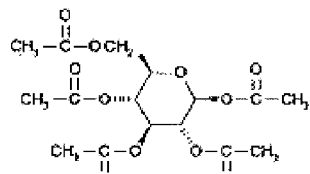
Figure 15A:
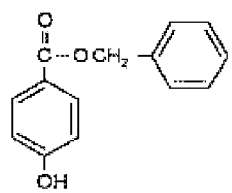
Figure 15A:
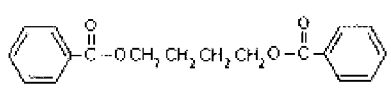
Figure 15A:
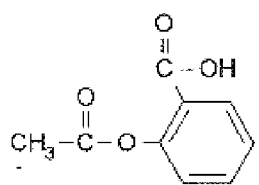
Figure 15B:
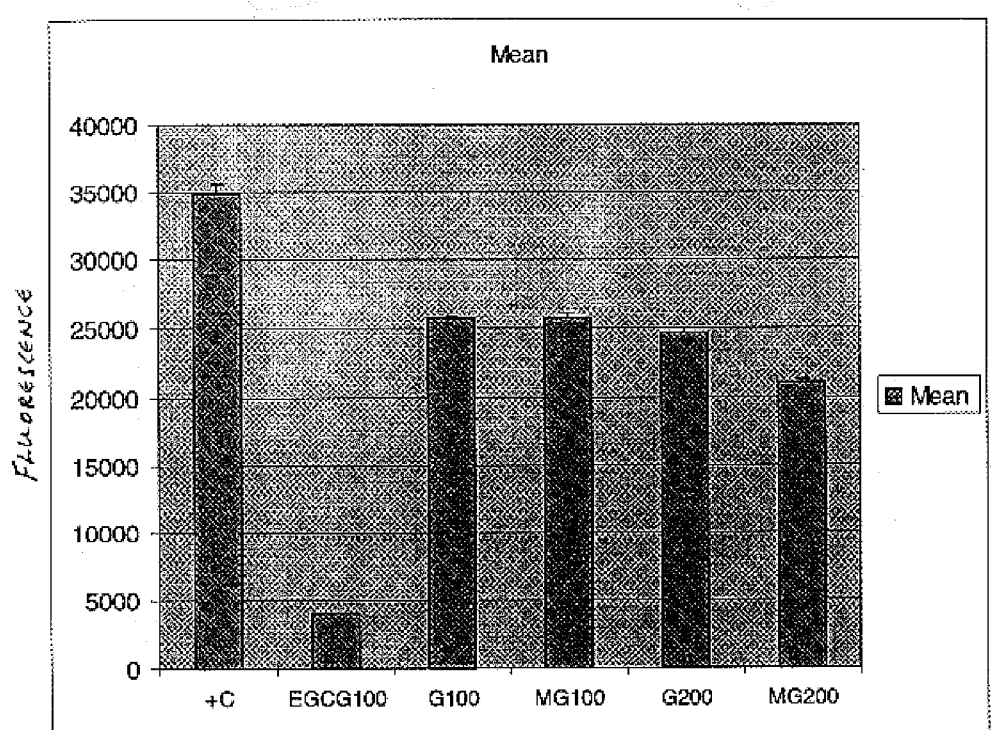
Figure 15B:
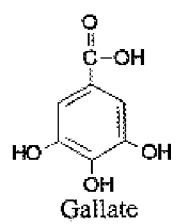
Figure 15B:
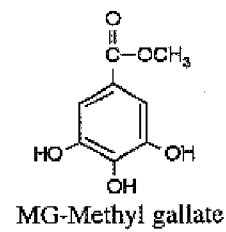
Figure 15C:
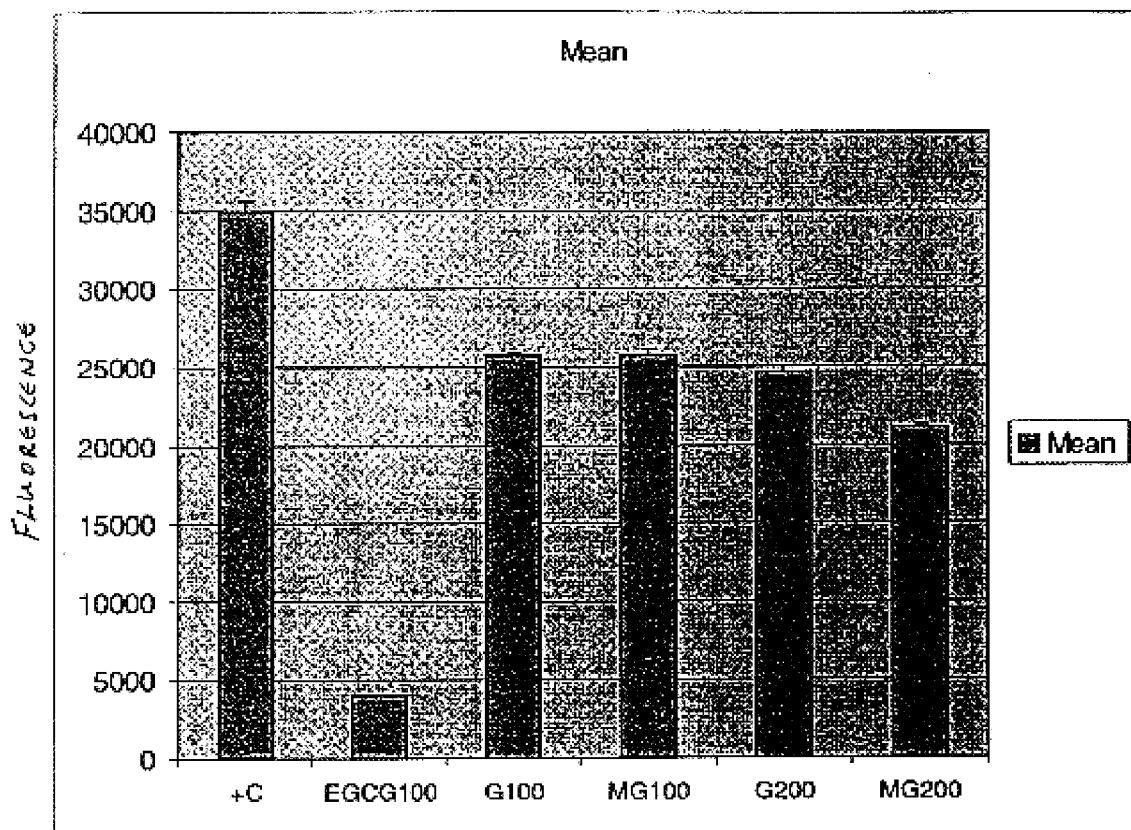
Figure 15C:
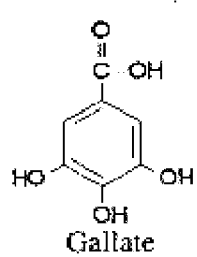
Figure 15C:
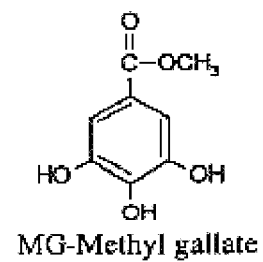

An ester bond-containing molecule has the potential to inhibit the proteasome activity. However, the ester-bond alone is insufficient for potent proteasome inhibition. For example, the simple compounds disclosed in FIGS. 15A & B contain an ester bond but they are weak proteasome inhibitors. Some binding groups on one or both sides of the ester bond are hereby shown to be necessary for inhibition; eg. methyl gallate is more potent than gallate in inhibition of the proteasome activity (FIG. 15B). Thus, the number of hydroxyls, or other groups, on one or both sides of the ester bond place the ester-bond in the appropriate proximity to the active site of the proteasome for inhibition of the proteasome.

EXAMPLE 6

Figure 16:
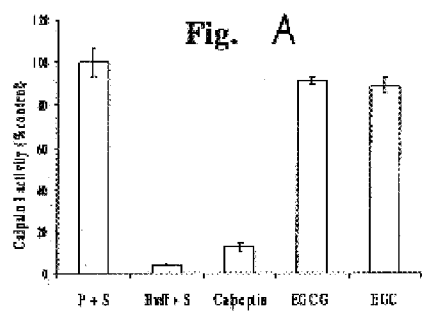
FIG. 16(A) The fluorogenic calpain I peptide substrate Suc-Leu-Tyr-AMC (S; 40 μM) is incubated with either a purified calpain I (P; 3 μg) or buffer (Buff) at 30° C. for 30 min with or without 10 μM calpeptin, EGCG or EGC, followed by measuring AMCs (the product), as described in the text. (B) T1 or T2 cells are treated with LLL at either 10 (A–C) or 50 μM (D, E), followed by Western blotting with indicated antibodies.(C) MCF-7 cells, pre-incubated with EGCG at an indicated concentration for 12 h, are incubation for additional 12 h with 20 μM Suc-Leu-Leu-Val-Tyr-AMC (the peptide substrate for the proteasomal chymotryptic activity), followed by measurement of AMCs in medium (as described in the grant and the manuscript). (D) Cell cycle-dependent p27 degradation. PCI-13 head and neck tumor cells are treated with aphidicolin (5 μg/ml) for 24 h (0 h), followed by release for up to 24 h. Aliquots of the cells are used for flow cytometry (A), Western blotting with p27 antibody (B) or in vitro p27 degradation assay (C). In C, 2 μl of in vitro-translated, [$^{35}$S]-labeled p27 protein (lane 1 in panel C) is incubated with 80 μg protein extract at 37° C. for 2 h, followed by gel electrophoresis and autoradiography. The labeled p27 band and a p27 cleavage product are indicated.
Figure 16:
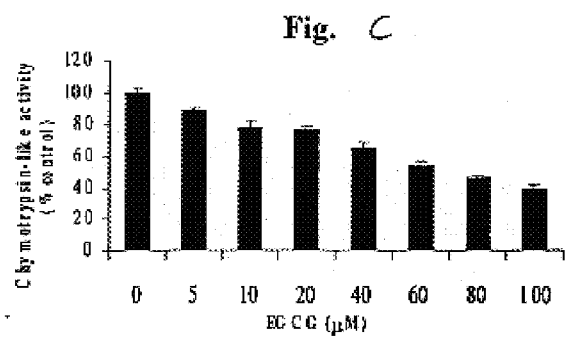
Figure 16:
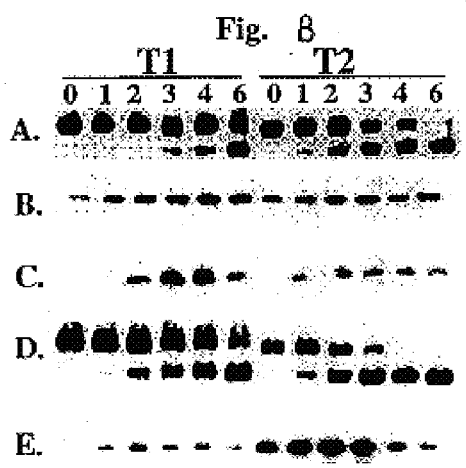
Figure 16:
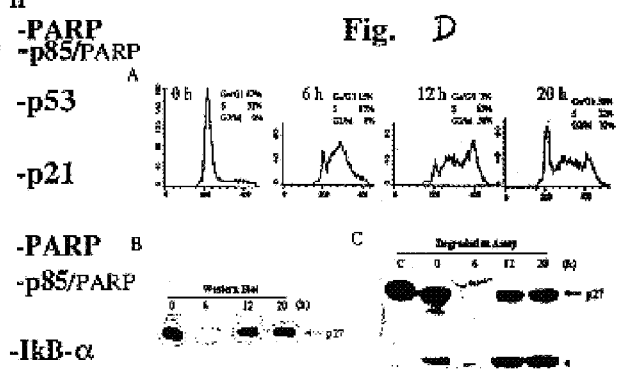

Inhibition by Tea Polyphenols of Proteasome Activity of: (a) Extracts of Breast Cancer MCF-7 Cells; (b) Three Mutant p53-Containing Breast Cancer Cell Lines With Low, Medium or High Levels of the Proteasome Activity; and (c) Three Pairs of Breast Normal and Cancer Cell Lines In (a), 20 µM of the peptide substrate for the proteasomal chymotryptic activity (Suc-Leu-Leu-Val-Tyr-AMC) is incubated with 5 µg of MCF-7 cell extract in the absence or presence of EGCG, EGC, ECG, EC, or their epimers at various concentrations (0–50 µM). A green or black tea polyphenol extract is used as a positive control (0–50 µg/ml). The reaction mixture is incubated at 37° C. for up to 2 h in 100 µl of assay buffer (20 mM Tris-HCl, pH 8.0), followed by measurement of the hydrolyzed 7-amido-4-methyl-coumarin (AMC) groups (the product) on VersaFluor™ fluorometer with excitation filter of 380 nm and an emission filter of 460 nm. From this experiment, potency of each tea polyphenol to inhibit the proteasomal chymotrypsin activity of MCF-7 cell extract is obtained and reported as IC$_{50}$ values. Data obtained using a human Jurkat T cell extract demonstrates that EGCG is the most potent proteasome inhibitor among all the tested polyphenols. Similarly, potencies of tea polyphenols to inhibit the proteasomal trypsin-like and peptidylglutamyl-peptide hydrolase (PGPH) activities are measured by using peptide substrates Z-Gly-Gly-Arg-AMC and Z-Leu-Leu-Glu-AMC, respectively. A purified 20S proteasome and the specific proteasome inhibitor clastolactacystin β-lactone (β-lactone) are used as controls in this experiment. To further demonstrate that the target of tea polyphenols is the 26S proteasome, the cellular proteasome is immunoprecipitated from the MCF-7 protein extract using a specific antibody to 20S proteasome subunit α6 antibody. The prepared proteasome immunoprecipitates are used for proteasome activity assay with or without a tea polyphenol. To study selectivity of tea polyphenols, their effects on calpain protease activity are determined. MCF-7 cell extract is incubated with a fluorogenic calpain I peptide substrate (Suc-Leu-Tyr-AMC; 40 µM) at 30° C. for 30 min in a buffer containing 50 mM Tris-HCl/pH 7.5, 50 mM NaCl, 5 mM L-cysteine, 5 mM β-mercaptoethanol, 5 mM CaCl$_2$ and 0.1% CHAPS, with or without a tea compound. calpain I and II as well as the specific calpain inhibitor calpeptin is used as control. Neither EGCG nor EGC at 10 µM inhibits a purified calpain I activity (FIG. 16A). Levels of the proteasomal chymotrypsin-like activity in mutant p53-containing human breast cancer cell lines: MDA-MB-231, MDA-MB-435, MDA-MB-468, BT-549, T-47D and Hs 578T, are measured. Based on the results, three of these breast cancer cell lines with low, medium and high levels of the chymotrypsin-like activity, respectively, are selected. Protein extracts (5–20 µg) of these three cell lines are then used for the cell-free proteasome activity assay in the presence of EGCG (vs. EGC) or ECG (vs. EC). From these studies, a relationship is determined between potency of EGCG (or ECG) and levels of cellular proteasomal activity in breast cancer cells. Human B-lymphoblastoid cell lines T1 (containing wild-type proteasome) and T2 (with a homozygous deletion of two proteasome subunits, LMP2 and LMP7) are used. T2 cells express higher basal levels of IκB-α and p53 proteins than T1 cells (FIG. 16B, panels E and B, compare two 0 hrs), consistent with the deletion mutation in the T2 cellular proteasome. Furthermore, T2 cells are more sensitive to proteasome inhibitor LLL-induced apoptosis, as judged by PARP cleavage, than T1 cells (FIG. 16B, panels A and D). Thus, cells containing lower proteasome activity are more sensitive to proteasome inhibition. Increased levels of IκB-α (from different basal levels) are observed in both T1 and T2 cells after LLL treatment (FIG. 16B, panel E), while more dramatic induction of p53 and p21 is observed in T1 than in T2 cells (FIG. 16B, panels B and C). As a control experiment for the proposed breast cancer studies, the proteasome activity levels and tea polyphenols' potency in T1 and T2 cells are measured. T2 cells are transfected with cDNA(s) encoding LMP2, LMP7 or both, and the effects on potency of tea polyphenols are examined. Mutant p53-containing breast cancer cell lines are treated with EGCG, followed by measurement of growth arrest and/or apoptosis. Three cell lines with different sensitivity (from low to high) to EGCG-induced growth arrest and/or apoptosis are also used. Protein extracts prepared from human breast normal vs. cancer cell lines are also used: Hs 578Bst vs. Hs 578T, Hs 605.Mg vs. Hs 605.T, and Hs 574.Sk vs. Hs 574.T. Basal levels of the proteasomal chymotrypsin-like activity and inhibitory potency of EGCG (EGC, ECG or EC) in protein extracts of these breast normal and cancer cell lines are compared. The in vitro data thus determined herein is compared to in vivo sensitivity of both normal and cancer breast cells to tea polyphenol treatment.

EXAMPLE 7

Potency and Selectivity of Tea Polyphenols to Inhibit Proteasomes in Intact Breast Cancer Cells.

MCF-7, the three mutant p53-containing breast cancer cell lines with low, medium or high levels of the proteasome activity (or the three breast cell lines with low to high sensitivity to EGCG-induced growth arrest and/or apoptosis), and at least one pair of human breast normal and cancer cell lines are used in this example. T1 and T2 cells (as well as T2 cells transfected with LMP2, LPM7 or both) are also used.

Specific proteasome (lactacystin, β-lactone) and calpain (calpeptin) inhibitors are used as controls. The in vivo potency of tea polyphenols to inhibit the proteasome activity in these cell lines is measured by: the cell-free proteasome activity assay using protein extracts prepared from cells pretreated with a tea polyphenol (a), inhibition of the proteasome activity in intact cells (b), accumulation of cellular p27 and Bax proteins (c), and cell-free p27 and Bax degradation assays using protein extracts from tea polyphenol-pretreated cells (d).

(a) The selected cell lines are treated with EGCG (vs. EGC) or ECG (vs. EC) at various concentrations (0–80 μM) for up to 96 h, followed by preparation of protein extracts and measurement of the proteasomal chymotrypsin-like, trypsin-like and PGPH activities and the calpain activity in cell-free assay. Cell lysate, prepared from MCF-7 cells pretreated with the tripeptide proteasome inhibitor LLnV, contains decreased levels of proteasome activity. Thus, a protein extract of breast cancer cells pretreated with EGCG also contains decreased levels of the proteasome activity.

(b) The peptide substrate for the proteasomal chymotrypsin-like activity, Suc-Leu-Leu-Val-Tyr-AMC, is used to measure the proteasome activity in intact Jurkat, MCF-7 and PC-3 cells, which is inhibitable by co-incubation with EGCG (FIG. 16C). A similar assay is performed to measure potency and selectivity of EGCG (vs. EGC) or ECG (vs. EC) in the selected cell lines. Briefly, cells are pretreated with a tea compound (0–80 μM) for 12 h, followed by incubation for additional 12 h with 20 μM of a peptide substrate for the proteasomal chymotrypsin-like, trypsin-like or PGPH activities or the calpain activity. After that, medium is collected and the liberated AMCs in the medium are measured by fluorometer to measure in vivo potency and selectivity of tea polyphenols.

(c) Pro-apoptotic protein Bax, but not the anti-apoptotic protein Bcl-2, is degraded by the proteasome activity present in a MCF-7 cell extract and a prostate cancer tissue extract. In addition, during proteasome inhibitor-induced apoptosis, Bax is accumulated in mitochondria while Bcl-2 is neither degraded nor cleaved. Thus, selective degradation of Bax by the proteasome is involved in tumor cell survival. In contrast, Bcl-2 but not Bax is degraded by the proteasome in human endothelial cells treated with tumor necrosis factor (TNF)-α, indicating that Bcl-2 degradation is important for TNF-α-induced tumor cell death. Therefore, cellular fate is decided by selective degradation by the proteasome between pro- and anti-apoptotic (or pro- and anti-proliferative) proteins. Understanding how and when the proteasome makes such a selection has great significance in the improvement of current cancer therapies. In this example we show that tea polyphenol treatment results in accumulation of anti-proliferative (or pro-apoptotic), but not pro-proliferative (or anti-apoptotic), proteins. This is supported by the documented antitumor activity of green tea. In particular, p27 (a proliferation inhibitor) and Bax (an apoptosis inducer) proteins, using p21 (proliferation inhibitor), Bcl-$X_S$ (apoptosis inducer), cyclin E (proliferation promoter), Bcl-2 (apoptosis inhibitor), and Bcl-$X_L$ (apoptosis inhibitor) are used. Breast cancer and normal cells are treated with a tea compound, followed by measurement of levels and localization of p27 and Bax (as well as some or all of the control proteins). Levels of these proteins are measured by indirect immunoperoxidase method (examined by flow cytometry) and Western blot analysis using whole cell extracts. Subcellular localization of these proteins is measured by immunocytochemistry and Western blot assay using isolated cytoplasmic, nuclear and mitochondrial fractions. To estimate levels of cross-contamination, the filter containing different cellular fractions is reblotted with specific antibodies to IκB-α, PARP, or cytochrome oxidase, three proteins localized in cytoplasmic, nuclear or mitochondrial compartments of a cell, respectively. If EGCG (or ECG) targets the degradation enzyme of p27 or Bax in vivo, half-lives of p27 or Bax proteins are be significantly increased after the treatment. Cells are preincubated for 12 h with EGCG, EGC, ECG or EC (0–80 μM), followed by pulse-chase labeling with [$^{35}$S]-methionine. In addition, treatment with a tea polyphenol increases levels of ubiquitinated p27 (or Bax) protein in these cells is shown by reimmunoprecipitation of p27 (or Bax) immunoprecipitates with an anti-ubiquitin antibody and by a coupled immunoprecipitation-Western blot assay using different antibodies.

(d) The cell-free p27 (FIG. 16D) and Bax degradation assays in which an in vitro-translated, [$^{35}$S]-labeled p27 or Bax protein can be degraded by a tumor cell protein extract, inhibitable by addition of a proteasome, but not the calpain, inhibitor. Aliquots of protein extracts of breast cells pretreated with a tea polyphenol are incubated with a labeled p27 or Bax protein at 37° C. for 2 h, followed by gel electrophoresis and autoradiography. Levels of the remaining labeled p27 or Bax, which are scanned and quantitated, inversely correlate to the levels of p27 or Bax degradation activity. Labeled p21, cyclin E and Bcl-2 proteins are used as controls in this experiment. The in vivo potencies of tea compounds to inhibit p27 and Bax degradation are compared to their in vivo and in vitro potencies to inhibit the proteasomal chymotrypsin-like activity. Next, it is shown that tea polyphenols selectively inhibit cellular proteasome activity and induce apoptosis in breast cancer, but not normal, cells.

EXAMPLE 8

To Correlate the Proteasome Inhibitory Potencies of Tea Polyphenols to Their Abilities to Inhibit Proliferation and/or Induce Apoptosis in Breast Cancer Cells.

Tea polyphenols have anti-proliferation and antitumor activity. To show that the anti-proliferation and antitumor activity of tea polyphenols is related to their ability to inhibit the proteasome activity that degrades growth suppressor proteins (i.e., p27, Bax) MCF-7, the three mutant p53-containing breast cancer cell lines with different proteasome activity levels, T1, T2 and T2 cells transfected with LMP2, LMP7 or both, and at least one pair of breast normal and cancer cell lines are treated with EGCG (vs. EGC) or ECG (vs. GC) at 0–80 $\mu$M for up to 96 h, followed by measurement of p27 (a) or Bax (b)-mediated downstream events.

(a) EGCG treatment increases p27 protein levels and so the functional significance of p27 is evaluated. At each time point, whole cell extracts and subsequently p27 immunoprecipitates are prepared. The p27 immunoprecipitates are immunoblotted with antibodies to the $G_1$ and S phase-specific cyclins (D, E and A) and cdks (2, 4 and 6). To determine whether p27 inhibits activities of its associated cdk kinases, immunoprecipitates prepared from antibodies to p27 or p27-associated cyclin or cdk protein are incubated with [$\gamma$-$^{32}$P]ATP and an in vitro substrate protein (histone H1 or a fusion RB protein). The phosphorylated products are analyzed by gel electropheresis and autoradiography. Since tea polyphenol-accumulated p27 inhibits cyclin D/cdk4/cdk6 or cyclin E/cdk2 kinase activities, RB becomes dephosphorylated. Hyperphosphorylated RB migrates more slowly in gels than the unphosphorylated RB, which can be measured by Western blotting. To show that the dephosphorylated RB binds to E2F and blocks its DNA-binding activity, gel retardation assay is performed. Further, effects of a tea polyphenol on cell cycle progression is determined by flow cytometry. The above experiments are repeated with breast cancer cells synchronized at $G_0/G_1$ (by serum starvation) or $G_1/S$ (by aphidicolin). The apoptotic effects of tea polyphenols is also measured (see b).

Colony formation in soft agar is determined in 0.3% Bacto Agar, 0.67×DMEM, and 6.7% heat-inactivated FCS overlaying a preformed 0.6% agar layer. Plates (35 mm in diameter) containing 1000 cells in agar are incubated at 37° C. in 5% $CO_2$, and colonies containing >30 cells are counted under microscope at 10, 12 and 14 days.

(b) Next, it is shown that the accumulated Bax protein interacts with Bcl-2 (or Bcl-$X_L$) in mitochondria (by performing the IP-Western assay) and Bax accumulation is associated with cytochrome c-mediated apoptosis. Release of cytochrome c is determined by Western analysis of both cytosolic and mitochondrial fractions. Processing/activation of caspase-3 and cleavage of PARP is measured by Western blot assay. Apoptosis is measured by sub-$G_1$ apoptotic peak production, nuclear condensation/fragmentation and TUNEL assay.

EXAMPLE 9

Molecular Mechanisms by Which Ester Bond-Containing Tea Polyphenols Inhibit Proteasome-Mediated Degradation Activity of p27 and Bax.

The effects of tea polyphenols on cell cycle or apoptosis are due to increased levels of p27 or Bax protein. Therefore, decreasing or increasing p27 (or Bax) protein levels makes breast cancer cells more resistant or sensitive to treatment with ester bond-containing tea compounds, respectively. In (a), reduce the levels of p27 by transfecting breast cancer cells with p27 antisense oligonucleotides. MCF-7 and another breast cancer cell line containing a high basal level of p27 (to be selected from Aim IIc) is transfected with 1 $\mu$M of p27 C-5-propyne-modified oligonucleotides 5'-UGGCUCUCCUGCGCC-3', with the corresponding mismatch oligonucleotide 5'-UCCCUUUGGCGCGCC-3' as a control. These cells are treated with EGCG (vs. EGC) or ECG (vs. EC) (0–80 $\mu$M) for up to 96 h, followed by measuring the proteasome activity levels (using a peptide substrate or a labeled p27; to examine whether the upstream event is affected), p27 expression/localization, the p27-associated cdk kinase activity, pRB phosphorylation status, E2F activity and cell cycle distribution as well as apoptotic events. Levels of Bax and p21 proteins are measured in these cells show the effect is p27-specific. In (b), breast cancer cells are transfected with Bax antisense phosphorothioate oligonucleotide 5'-TGCTCCCCGGACCCGTCCAT-3', with the corresponding sense oligo 5'-ATGGACGGGTCCGGGGAGCA-3' as a control. After tea polyphenol treatment, the proteasome activity levels (using a peptide substrate or a labeled Bax), Bax expression and localization, Bax-Bcl-2 interaction, cytochrome c release, caspase activation, PARP cleavage, and apoptosis, are measured. Levels of p27 and Bcl-2 is measured in these cells as controls. In c, we show overexpression of p27 in breast cancer cells affects cellular sensitivity to treatment of tea polyphenols. Full-length p27 cDNA is subcloned into the pcDNA3.0 expression vector, and the resulting construct is used to transfect MCF-7 or another breast cancer cell line containing low basal p27 level using GenePORTER Transfection Reagent. The pcDNA3.0 vector alone is used as a control. The transiently transfected cells are treated with a tea polyphenol for additional 96 h. At each time point, proteasome activity levels, p27 expression/localization, and the p27 downstream cell cycle and apoptotic events, are measured. Similarly, in (d), overexpression of Bax in breast cancer cells is shown to affect sensitivity to tea polyphenols by measuring proteasome activity levels, Bax expression/localization, and the Bax downstream events. In addition, the p27 or Bax cDNAs are subcloned into the pcDNA 3.0 vector containing a gene that confers resistance to G418. The resulting constructs are introduced individually by electroporation into the selected breast cancer cell lines. As a control, cells are transfected with the vector alone. Following electroporation, cells are selected by addition of G418.

EXAMPLE 10

Relationship Between Antitumor and Proteasome-Inhibitory Activities of Tea Polyphenols in vivo Using Nude Mice Bearing Human Breast Tumors Treatment of drinking water with green tea, a green tea polyphenol extract or EGCG, or direct injection into tumors of a solution containing a green tea polyphenol extract or EGCG, inhibits breast or other tumor growth in nude mice. In (a) it is shown that antitumor activity of tea polyphenols correlates to their potency to inhibit the proteasome activity. All mice receive a 90-day slow-release subcutaneous (s.c.) estrogen pellet (Innovative Research) in the anterior flank 7 days before tumor inoculation. In Experiment 1, mice (5 per group) are pre-fed with a solution of EGCG, EGC, ECG, EC, a green tea extract (1, 10, and 50 mg/kg) or water three times per week for 2 weeks, followed by s.c. implanting human breast MCF-7 tumor cells in nude mice above the right and left flanks ($10^7$ cells per flank). When tumors in the control group reach ~1000 $mm^3$ the experiment is terminated. In Experiment 2, on day zero, MCF-7 cells are injected s.c. into the left and right flanks of mice ($10^7$ cells per flank). The s.c. growing tumors are staged one to three weeks after implantation, and healthy mice bearing 50 to 100 $mm^3$ tumors (estimated from caliper measurements) are randomized into test groups of 5 mice each. A solution of EGCG, EGC, ECG, EC, a green tea extract (0.3, 1 and 3 mg in 0.1 ml of water) or water is directly injected into the tumors once a day. The experiment ends when tumors in the control group reach ~1000 $mm^3$. Evaluation of the antitumor activity of tea polyphenols is determined by measuring the change in tumor size of the treated group compared to the control group. Statistical comparisons are made using the JMP IN 3 Software package. Biochemical end points. After animals are sacrificed, the tumor tissues are aliquoted and tissue extracts are prepared (frozen at −80° C.). The proteasome activity assay is performed with a peptide substrate or a labeled p27 or Bax protein as substrate. Levels of p27 and Bax protein in tumor tissues are measured by Western blotting and immunohistochemistry. Increased p27 levels are found in tumors from mice pre-fed or injected with EGCG: the p27 levels is then compared to the proteasome-mediated p27 degradation activity levels in these samples. p27-associated cdk activity and RB phosphorylation status as well as apoptosis (by TUNEL) are determined. Increased Bax protein levels are found, which correlate with the levels of Bax degradation activity. Bax localization (by immunohistochemistry), processing of caspase-3, cleavage of PARP (by Western blotting) and apoptosis (by TUNEL) are then measured. The proteasome-inhibitory potencies of tea polyphenols are thereby related to their antitumor activities and it is shown that ester bond-containing tea polyphenols directly target the proteasome in tumors. A synthetic dipeptidyl proteasome inhibitor inhibited the growth of the human lung tumor in nude mice, associated with direct inhibition of the proteasome activity, accumulation of p27 and p21, and induction of apoptosis in tumors.

In (b), it is shown that cellular proteasome activity levels affect the in vivo response of breast tumors to tea polyphenol treatment. Three mutant p53-containing breast cancer cell lines with low to high proteasome levels (or the three breast cancer cell lines with low to high sensitivity to in vitro EGCG treatment) are used, and the same two experiments described in (a) are preformed. In (c), the in vivo target of EGCG or ECG is shown to be the p27 (or Bax) degradation enzyme by using breast cancer cells stably overexpressing p27 or Bax.

While the invention has been described in terms of various preferred embodiments, those skilled in the art will recognize that various modifications, substitutions, omissions and changes can be made without departing from the spirit of the present invention. Accordingly, it is intended that the scope of the present invention be limited solely by the scope of the following claims.

What is claimed is:

1. A method for inhibiting the proteasomal chymotrypsin activity but not the proteasomal trypsin activity in a cell, comprising contacting the cell with an effective amount of a polyphenol having an ester bond that has a susceptibility to nucleophilic attack, wherein the polyphenol compound is

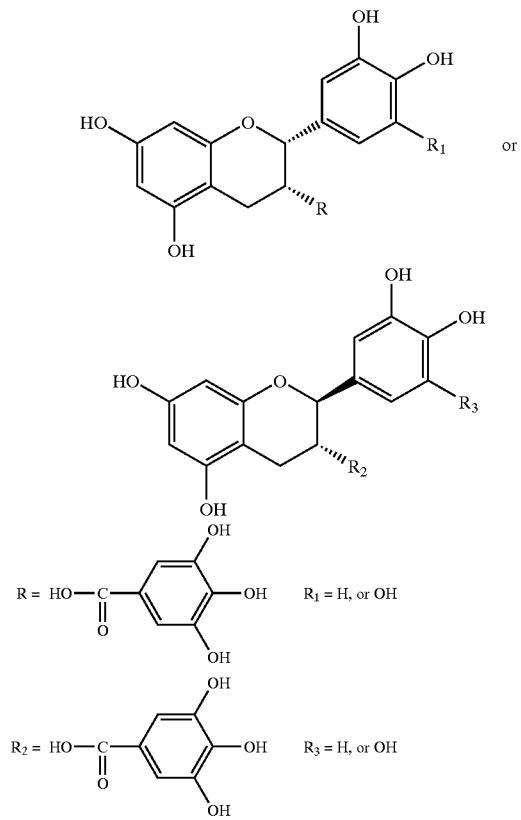

and verifying that proteasomal chymotrypsin activity has been inhibited.

2. A method for inhibiting the proteasomal chymotrypsin activity but not the proteasomal trypsin activity in a cell, comprising contacting the cell with an effective amount of a polyphenol having an ester bond that has a susceptibility to nucleophilic attack;

wherein the polyphenol ester has a structure selected from the group consisting of:

(1)

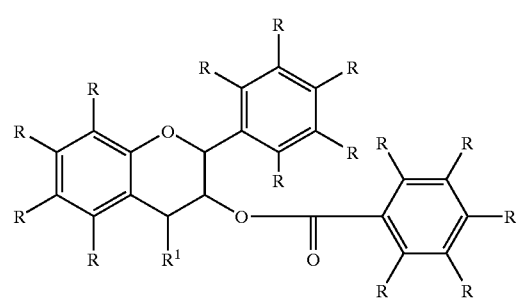

(2)
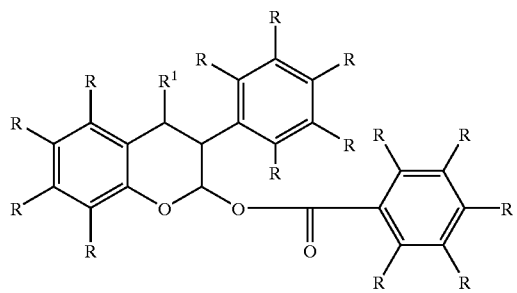
(3)
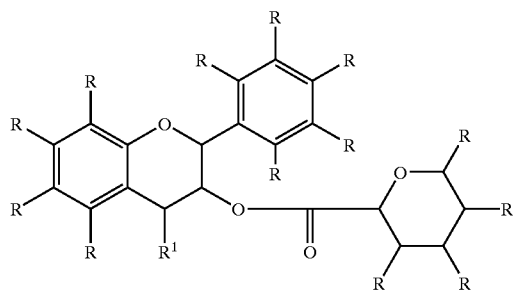
(4)
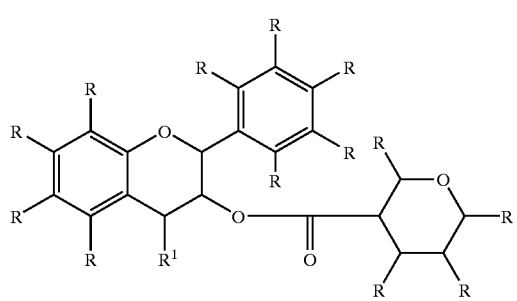
(5)
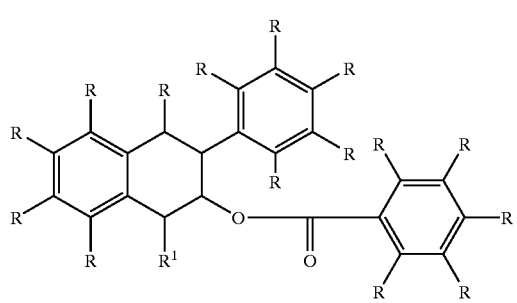
(6)
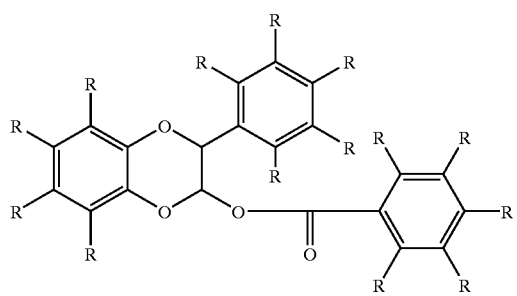
(7)
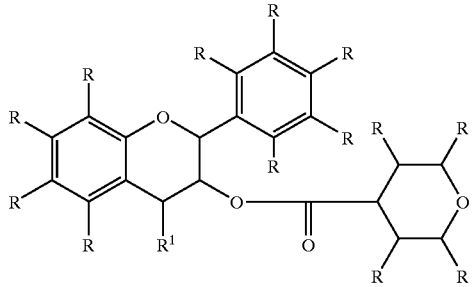
(8)
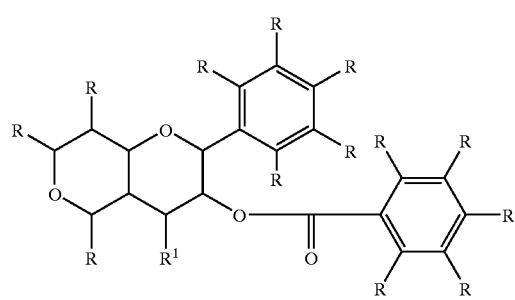
(9)
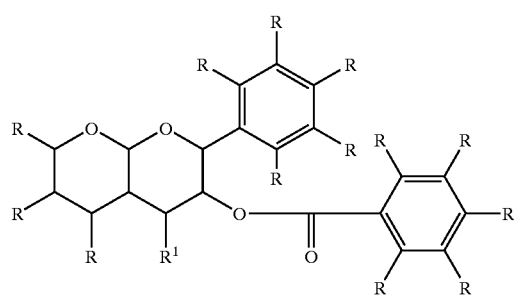
(10)
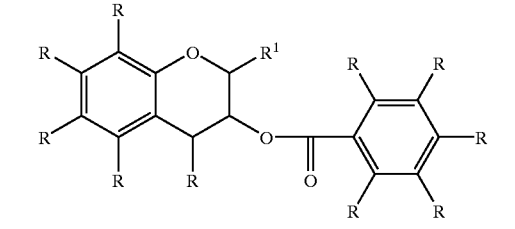
(11)
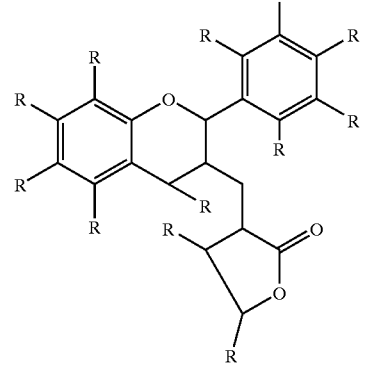

-continued
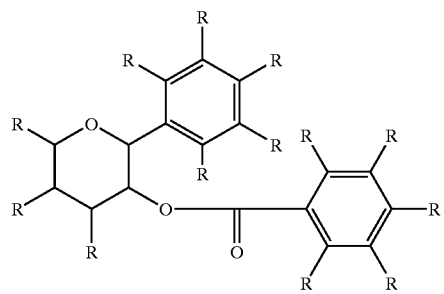
(12)
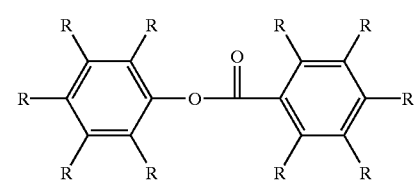
(13)
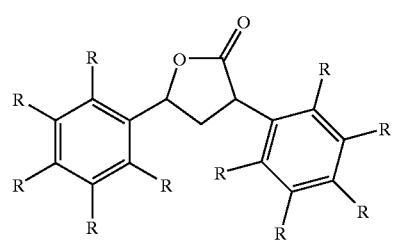
(14)
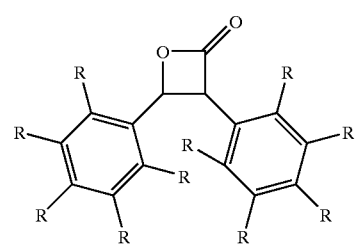
(15)
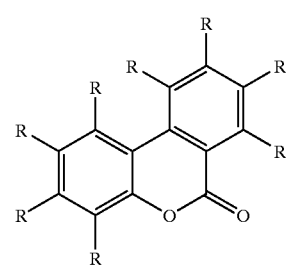
(16)
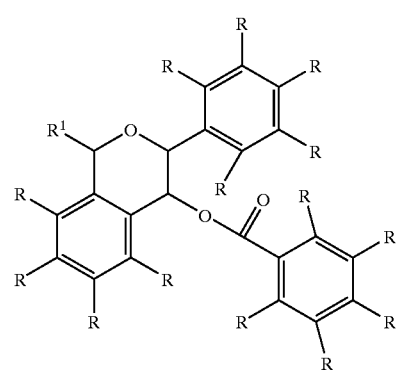
(17)
-continued
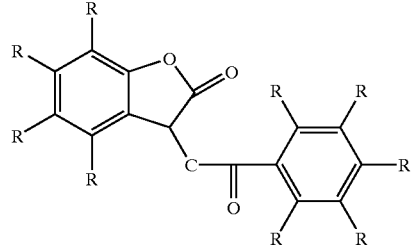
(18)
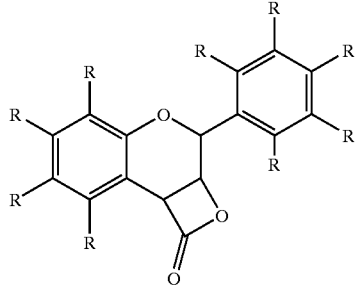
(19)
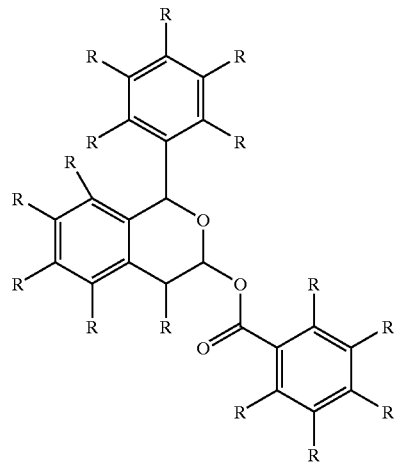
(20)
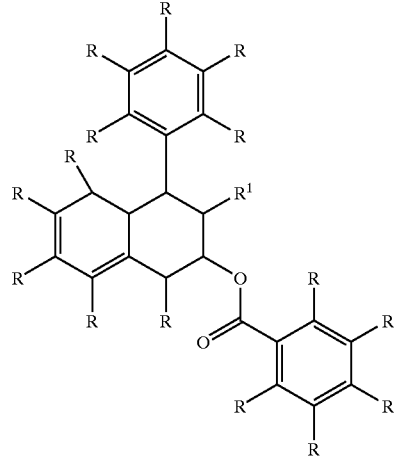
(21)

(22) 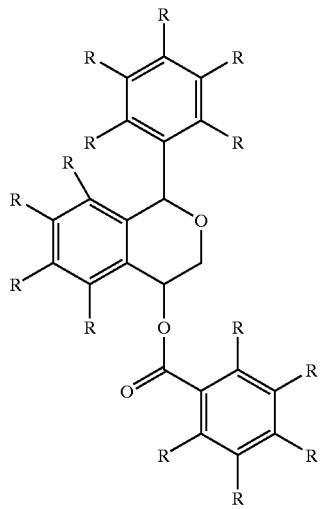

(23) 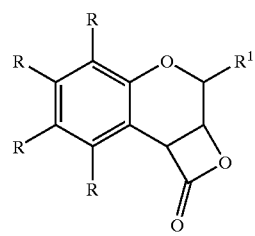

(24) 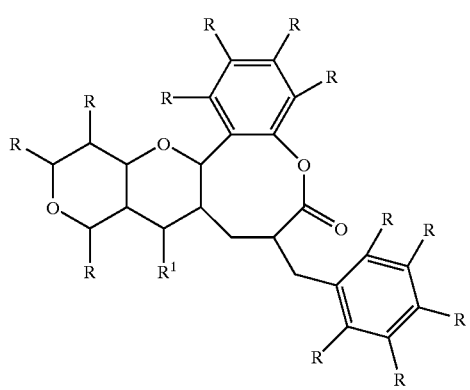

(25) 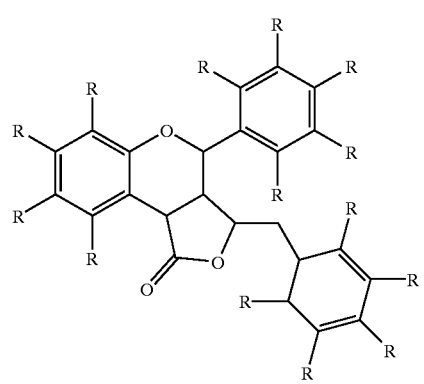

(26) 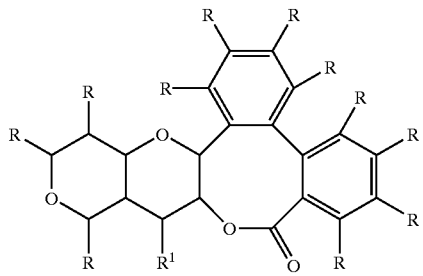

(27) 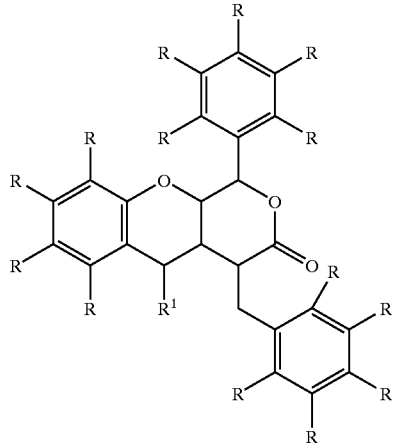

(28) 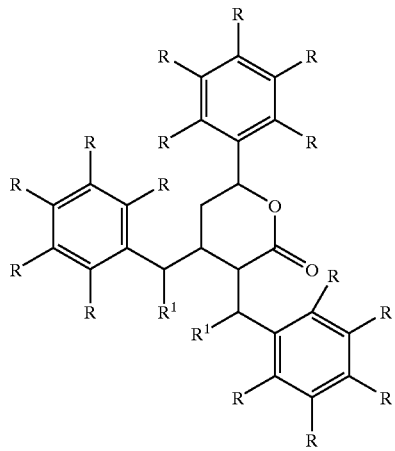

wherein each R is independently —H, —OH, —NH, —OMe, —CH$_2$OH, —CH$_2$NH$_2$, or -gallate; and wherein each R' is independently =O, —H, —OH, —HN$_2$, —OMe, —CH$_2$OH, —CH$_2$NH$_2$, or -gallate; and verifying the proteasomal chymotrypsin activity has been inhibited.

3. A method for treating a patient having a tumor comprised of cells exhibiting proteosomal chymotrypsin or chymotrypsin-like activity, comprising administering to said patient an effective amount of the composition of claim 2.

4. The method of claim 3, wherein the patient has been diagnosed with breast cancer or prostate cancer.

5. A method for inhibiting the proteasomal chymotrypsin activity but not the proteasomal trypsin activity in a cell, comprising contacting the cell with an effective amount of a compound having the formula:

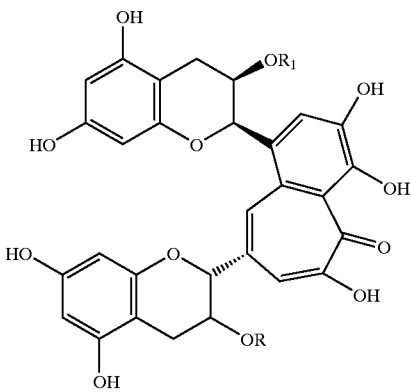

wherein R and $R_1$ are each independently —H or -gallate; and verifying that proteasomal chymotrypsin activity has been inhibited.

6. A method for inhibiting the proteasomal chymotrypsin activity but not the proteasomal trypsin activity cell in a patient having a cancer, comprising administering to the patient an effective amount of a compound having the formula:

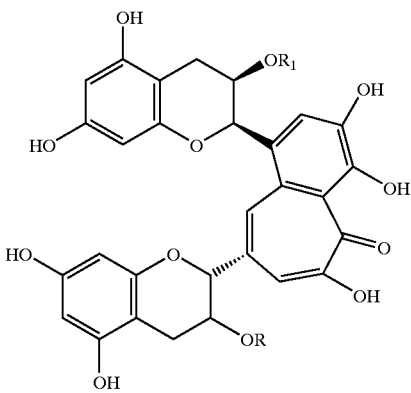

wherein R and $R_1$ are each independently —H or -gallate or a pharmaceutically-acceptable salt thereof; and observing an effect of proteasomal chymotrypsin inhibition in the patient.

7. A method for inhibiting selectively proteasomal chymotrypsin or chymotypsin-like activity in a neoplastic cell comprising contacting a neoplastic cell exhibiting chymotrypsin or chymotrypsin-like activity with an effective amount of at least one phenolic substance which bears a carboxylic acid ester bond that is susceptible to nucleophilic attack, or an analog thereof, wherein the phenolic substance is

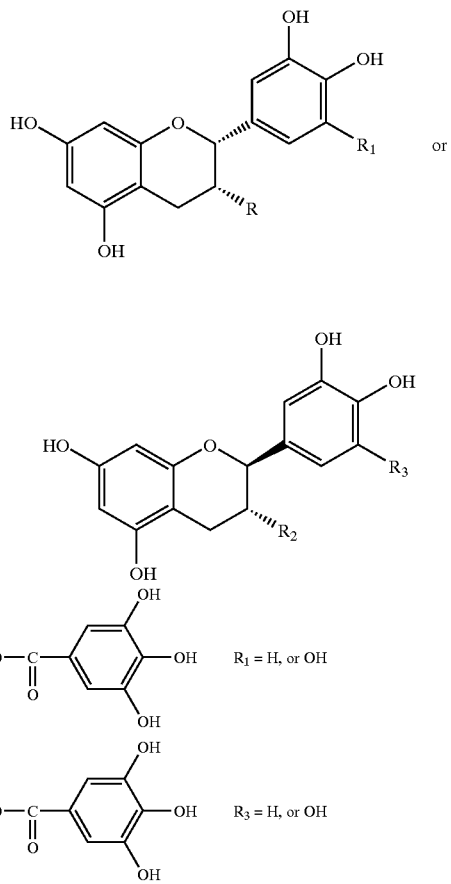

or combinations thereof.

8. A method for inhibiting selectively proteasomal chymotrypsin or chymotypsin-like activity in a neoplastic cell comprising contacting a neoplastic cell exhibiting chymotyrpsin or chymotyrpsin-like activity with an effective amount of at least one phenolic substance which bears a carboxylic acid ester bond that is susceptible to nucleophilic attack, or an analog thereof, wherein the analog of the phenolic substance is selected from at least one compound of the formula (1)–(28), in which R can be H, —OH, —NH$_2$, —OCH$_3$, —CH$_2$OH, —CH$_2$NH$_2$, or -gallate and R' can be the same as or different from R and, in addition, together with the carbon atom to which it is attached, can be C=O.

9. The method of claim 8 in which any proteasomal trypsin or trypsin-like activity exhibited by the neoplastic cell is substantially unaffected.

10. The method of claim 7 in which the neoplastic cell is present in an animal.

11. The method of claim 8 in which the neoplastic cell is present in an animal.

12. A method for arresting a tumor cell at a $G_1$-phase or inducing tumor cell apoptosis comprising contacting a tumor cell with an effective amount of an analog of a phenolic substance found in tea, wherein said analog of the phenolic substance is selected from at least one compound of the formula (1)–(28), in which R can be H, —OH, —$NH_2$, —$OCH_3$, —$CH_2OH$, —$CH_2NH_2$, or -gallate and R' can be the same as or different from R and, in addition, together with the carbon atom to which it is attached, can be C=O.

13. The method of claim 7 in which any proteasomal trypsin or trypsin-like activity exhibited by the neoplastic cell is substantially unaffected.

14. The method of claim 12 in which the tumor cell exhibits chymotrypsin or chymotrypsin-like activity.

15. The method of claim 12 in which the tumor cell is present in an animal.

* * * * *

UNITED STATES PATENT AND TRADEMARK OFFICE
CERTIFICATE OF CORRECTION

PATENT NO.     : 6,713,506 B2
DATED          : March 30, 2004
INVENTOR(S)    : Q. Ping Dou, Sangkil Nam and David M. Smith It is certified that error appears in the above-identified patent and that said Letters Patent is hereby corrected as shown below:

Column 3,
Line 19, "Western bot" should read -- Western blot --.

Column 5,
Line 24, "they are show to be" should read -- they are shown to be --.

Column 9,
Line 38, "supernant" should read -- supernatant --.

Column 10,
Line 67, "highly specifica and" should read -- highly specific and --.

Column 11,
Line 66, "is also be attacked" should read -- can also be attacked --.

Column 12,
Line 56, "chymothypsin" should read -- chymotrypsin --.

Column 13,
Line 15, "10 $\mu$M of ECGC" should read -- 10 $\mu$M of EGCG --.
Line 38, "concentraition" should read -- concentration --.
Line 46, "their G1 population" should read -- their $G_1$ population --.

Column 15,
Line 46, "theaflavins such theaflavin" should read -- theaflavins such as theaflavin --.

Column 16,
Line 47, "tea compound. calpain" should read -- tea compound. Calpain --.

Column 17,
Line 39, "transfected with LMP2, LPM7" should read -- transfected with -- LMP2, LMP7 --.

Column 18,
Line 53, "proteins are be significantly" should read -- proteins are significantly --.

UNITED STATES PATENT AND TRADEMARK OFFICE
CERTIFICATE OF CORRECTION

PATENT NO.   : 6,713,506 B2
DATED        : March 30, 2004
INVENTOR(S)  : Q. Ping Dou, Sangkil Nam and David M. Smith It is certified that error appears in the above-identified patent and that said Letters Patent is hereby corrected as shown below:

Column 22,
Line 11, Structure appears as:                should read

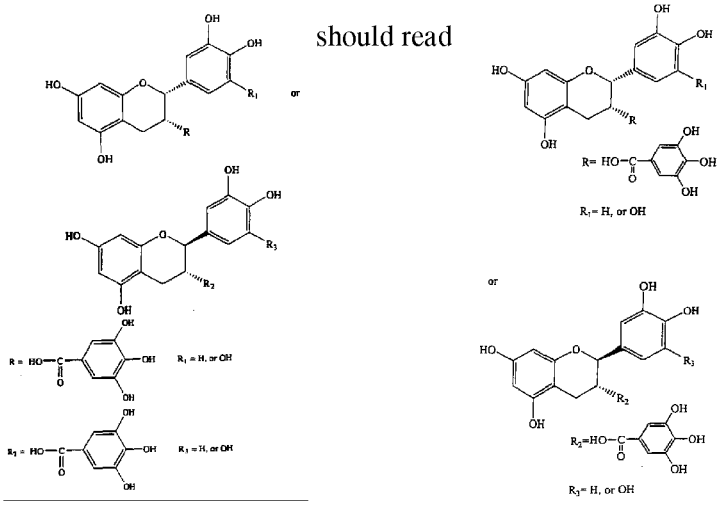

Column 29,
Line 30, "activity cell in a" should read -- activity in a cell in a --.
Line 61, "or chymotypsin-like activity" should read -- or chymotrypsin-like activity --.

Column 30,
Line 45, "or chymotypsin-like activity" should read -- or chymotrypsin-like activity --.

Signed and Sealed this

Fifth Day of October, 2004

JON W. DUDAS
*Director of the United States Patent and Trademark Office*